US012636356B2

(12) United States Patent　　　　(10) Patent No.:　US 12,636,356 B2
Nagy et al.　　　　　　　　　　　　(45) Date of Patent:　May 26, 2026

(54) HIGH DOSE SHIGELLA VACCINE PREPARATION

(71) Applicant: EVELIQURE BIOTECHNOLOGIES GMBH, Vienna (AT)

(72) Inventors: Eszter Nagy, Vienna (AT); Tamás Henics, Vienna (AT); Petra Girardi, Vienna (AT); Irene Neuhauser, Vienna (AT); Shushan Harutyunyan, Vienna (AT); Gábor Nagy, Sopron (HU); Valeria Szijarto, Vienna (AT)

(73) Assignee: EVELIQURE BIOTECHNOLOGIES GMBH, Vienna (AT)

( * ) Notice: Subject to any disclaimer, the term of this patent is extended or adjusted under 35 U.S.C. 154(b) by 485 days.

(21) Appl. No.: 18/031,218

(22) PCT Filed: Sep. 24, 2021

(86) PCT No.: PCT/EP2021/076378
§ 371 (c)(1),
(2) Date: Apr. 11, 2023

(87) PCT Pub. No.: WO2022/078732
PCT Pub. Date: Apr. 21, 2022

(65) Prior Publication Data
US 2023/0372462 A1　　Nov. 23, 2023

(30) Foreign Application Priority Data

Oct. 14, 2020　(EP) ..................................... 20201844

(51) Int. Cl.
*A61K 39/02*　　(2006.01)
*A61K 39/112*　　(2006.01)
*A61P 37/04*　　(2006.01)
*A61K 39/00*　　(2006.01)

(52) U.S. Cl.
CPC .......... *A61K 39/0283* (2013.01); *A61P 37/04* (2018.01); *A61K 2039/522* (2013.01); *A61K 2039/523* (2013.01); *A61K 2039/545* (2013.01)

(58) Field of Classification Search
None
See application file for complete search history.

(56) References Cited

FOREIGN PATENT DOCUMENTS

| EP | 3138741 A1 | 3/2017 |
| WO | WO 2014/037440 | 3/2014 |

OTHER PUBLICATIONS

Lu et al(Int J Mol Sci. Apr. 13, 2024; vol. 25:1-25.).*
Girardi, P. et al., "Evaluation of the Safety, Tolerability and Immunogenicity of ShigETEC, an Oral Live Attenuated *Shigella*-ETEC Vaccine in Placebo-Controlled Randomized Phase Trial," *Vaccines*, 10 (2022): 1-15.

Niyogi, S. K. et al., "Prevalence of the *sat, set* and *sen* genes among diverse serotypes of *Shigella flexneri* strains isolated from patients with acute diarrhoea," *Clin Microbiol Infect*, 10 (2004): 574-576.
International Search Report and Written Opinion issued in International Patent Application No. PCT/EP2021/076378, dated Nov. 30, 2021.
Ranallo, R. T. et al., "Immunogenicity and characterization of WRSF2G 11: A second generation live attenuated *Shigella flexneri* 2a vaccine strain," *Vaccine*, 25 (2007): 2269-2278.
Bourgeois, A. L. et al., "Status of vaccine research and development for enterotoxigenic *Escherichia coli*," *Vaccine*, 34 (2016): 2880-2886.
Cummings, H. S. et al., "Translation Initiation Factor IF1 is Essential for Cell Viability in *Escherichia coli*," *Journal of Bacteriology*, 176.1 (1994): 198-205.
Datsenko, K. A. et al., "One-step inactivation of chromosomal genes in *Escherichia coli* K-12 using PCR products," *PNAS*, 97.12 (2000): 6640-6645.
Extended European Search Report issued in European Patent Application No. 20201844.6, dated Mar. 31, 2021.
Fiorentino, M. et al., "Effect of Wild-Type *Shigella* Species and Attenuated *Shigella* Vaccine Candidates on Small Intestinal Barrier Function, Antigen Trafficking, and Cytokine Release," *PLOS ONE*, 9.1 (2014): e85211, 1-11.
Kotloff, K. L. et al., "*Shigella flexneri* 2a Strain CVD 1207, with Specific Deletions in *virG, sen, set*, and *guaBA*, is Highly Attenuated in Humans," *Infection and Immunity*, 68.3 (2000): 1034-1039.
Kotloff, K. L. et al., "Deletion in the *Shigella* Enterotoxin Genes Further Attenuates *Shigella flexneri* 2a Bearing Guanine Auxotrophy in a Phase 1 Trial of CVD 1204 and CVD 1208," *The Journal of Infectious Diseases*, 190 (2004): 1745-1754.
Kotloff, K. L. et al., "Safety and Immunogenicity of CVD 1208S, a Live, Oral ΔguaBA Δsen Δset *Shigella flexneri* 2a Vaccine Grown on Animal-Free Media," *Human Vaccines*, 3.6 (2007): 268-275.
Levine, M. M. et al., "Clinical trials of *Shigella* vaccines: two steps forward and one step back on a long, hard road," *Nat Rev Microbiol.*, 5.7 (2007): 540-553.
Medeiros, P. H. Q. S. et al., "A bivalent vaccine confers immunogenicity and protection. Against *Shigella flexneri* and enterotoxigenic *Escherichia coli* infections in mice," *Nature*, 30 (2020): 1-5.
Noriega, F. R. et al., "Strategy for Cross-Protection among *Shigella flexneri* Serotypes," *Infection and Immunity*, 67.2 (1999): 782-788.
PCT International Search Report issued in PCT International Patent Application No. PCT/EP2021/076378, mailed Jun. 28, 2023.
PCT International Search Report and Written Opinion issued in PCT International Patent Application No. PCT/EP2021/076378, mailed Nov. 30, 2021.
PCT International Preliminary Report on Patentability issued in PCT International Patent Application No. PCT/EP2021/076378, mailed Jul. 6, 2023.
Ranallo, R. T. et al., "Two live attenuated *Shigella flexneri* 2a strains WRSf2G12 and WRSf2G15: A new combination of gene deletions for 2nd generation live attenuated vaccine candidates," *Vaccines*, 30 (2012): 5159-5171.

(Continued)

*Primary Examiner* — Jennifer E Graser
(74) *Attorney, Agent, or Firm* — pH IP Law

(57) ABSTRACT

A *Shigella* vaccine preparation comprising 10E8-10E12 CFU of a live, genetically attenuated *Shigella flexneri* strain that comprises a chromosomal deletion of setBA and which is non-invasive as determined by the Sereny test and an in vitro invasion assay using HeLa cells, wherein the strain comprises an endogenous invasion plasmid that is genetically engineered to incorporate a heterologous expression construct expressing a pathogen-specific antigen.

11 Claims, 13 Drawing Sheets

Specification includes a Sequence Listing.

(56) References Cited

OTHER PUBLICATIONS

Schuch, R. et al., "Virulence Plasmid Instability in *Shigella flexneri* 2a is Induced by Virulence Gene Expression," *Infection and Immunity*, 65.9 (1997): 3686-3692.

Serény, B., Experimental Shigella Keratoconjunctivitis, *Acta Microbiol Acd Sci Hung*, 2.3 (1955): 293-296.

Taxt, A. M. et al., "Towards Rational Design of a Toxoid Vaccine against the Heat-Stable Toxin of *Escherichia coli*," *Infection and Immunity*, 84.4 (2016): 1239-1249.

Tribble, D. R. et al., "Resistant pathogens as causes of traveller's diarrhea globally and impact(s) on treatment failure and recommendations," *Journal of Travel Medicine*, 24.1 (2017): S6-S12.

Van de Verg, L. L. et al., "Antibody and Cytokine Responses in a Mouse Pulmonary Model of *Shigella flexneri* Serotype 2a Infection," *Infection and Immunity*, 63.5 (1995): 1947-1954.

Wei, J. et al., "Complete Genome Sequence and Comparative Genomics of *Shigella flexneri* Serotype 2a Strain 2457T," *Infection and Immunity*, 71.5 (2003): 2775-2786.

Wood, P. K. et al., "Comparison of DNA Probes and the Sereny Test for Identification of Invasive Shigella and *Escherichia coli* Strains," *Journal of Clinical Microbiology*, 24.3 (1986): 498-500.

* cited by examiner

ST-N12S    ...ENGPGPNSSNYCCELCCSPACTGCY

Fig. 3
A
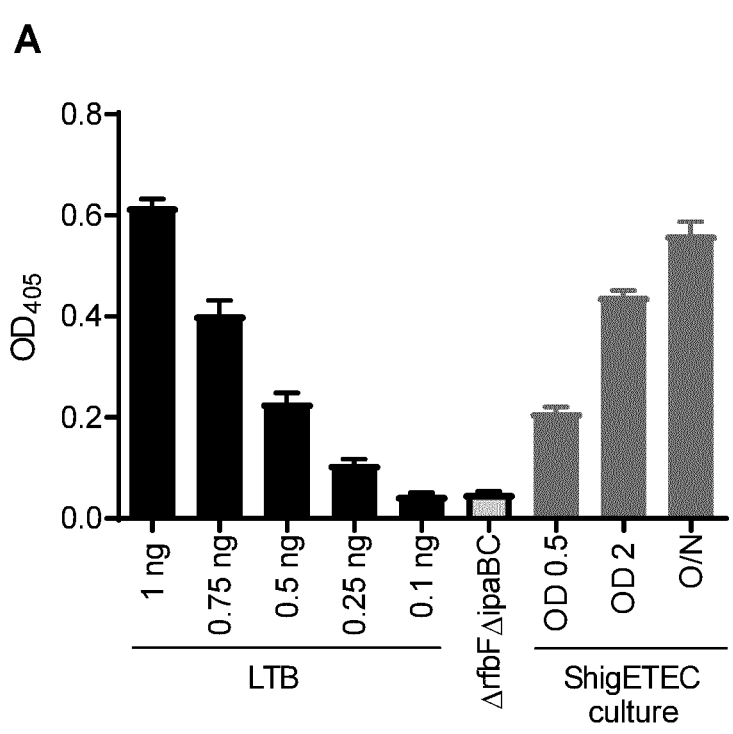
B
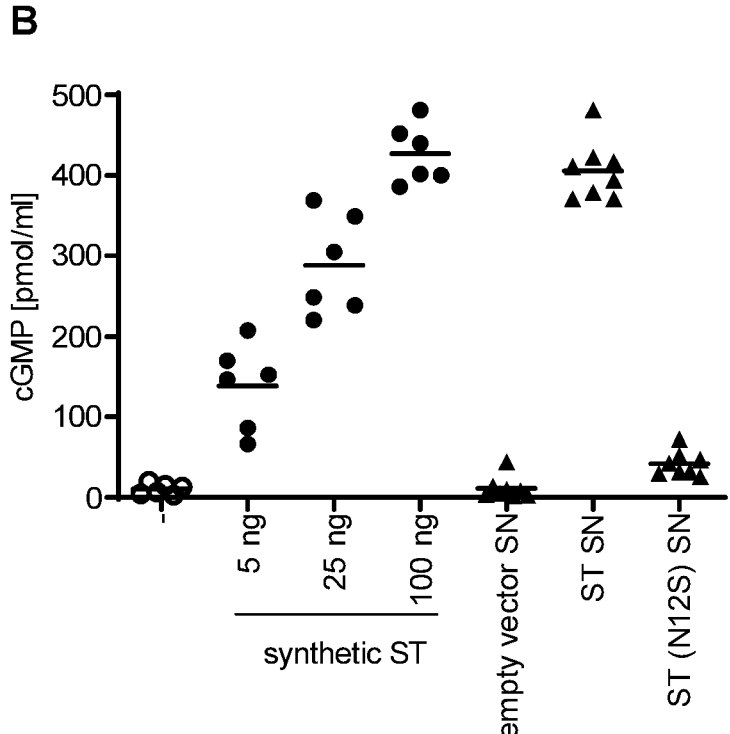

Fig. 4
A
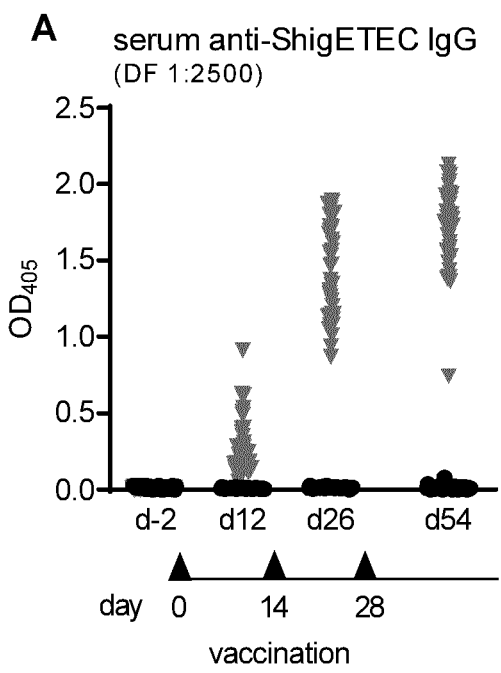
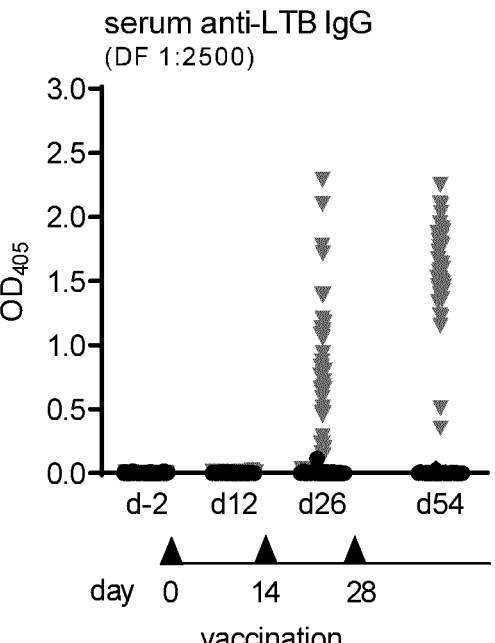
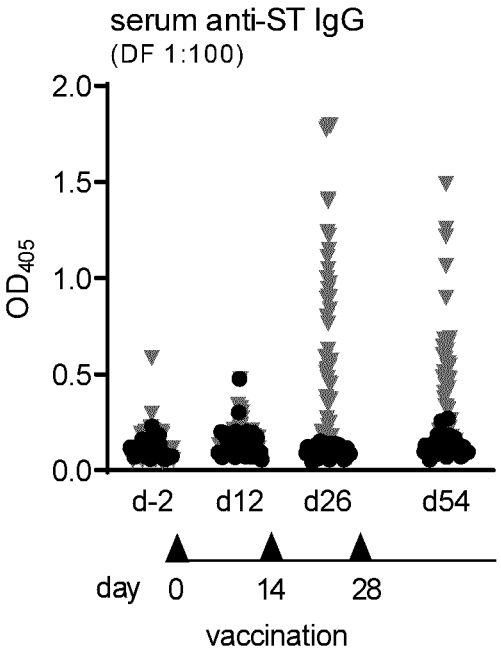

Fig. 4
B
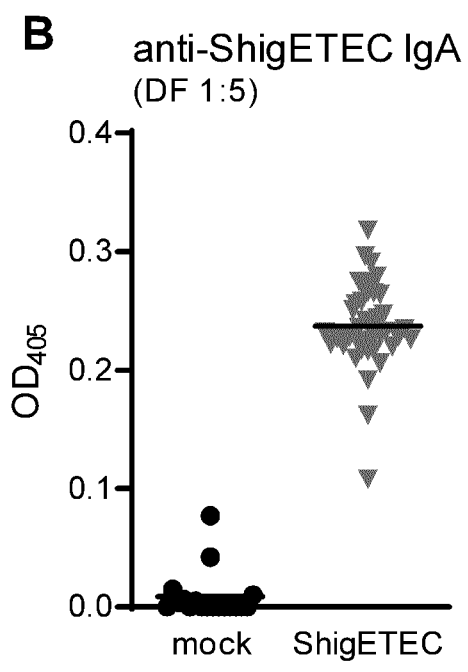
anti-ShigETEC IgA
(DF 1:5)
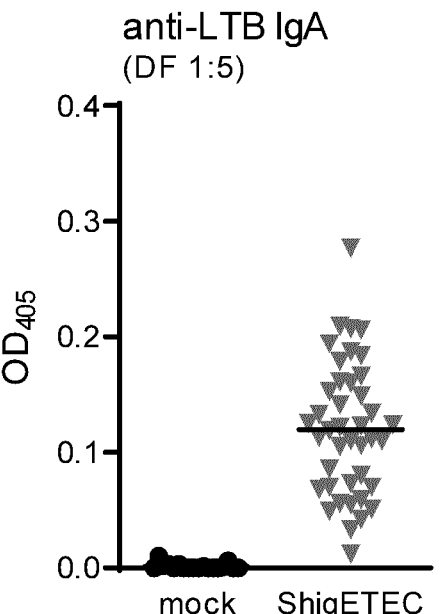
anti-LTB IgA
(DF 1:5)
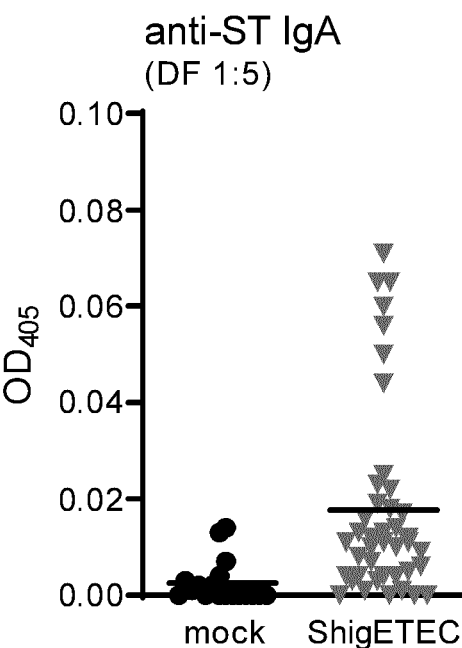
anti-ST IgA
(DF 1:5)

Figure 6:
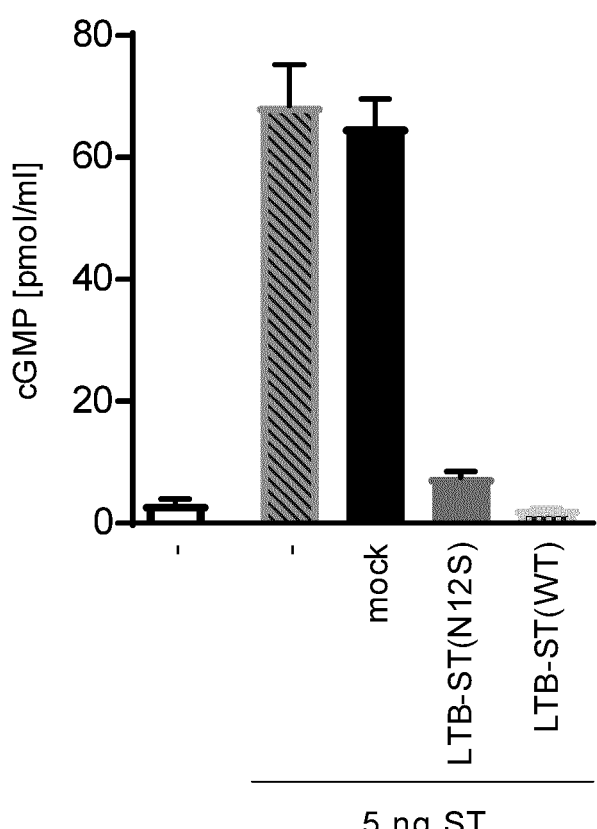

Fig. 6
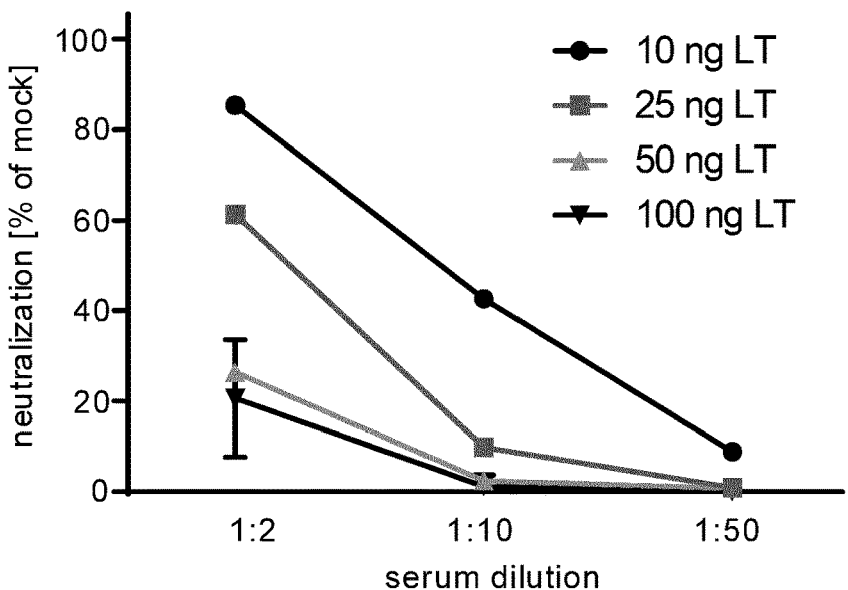
A
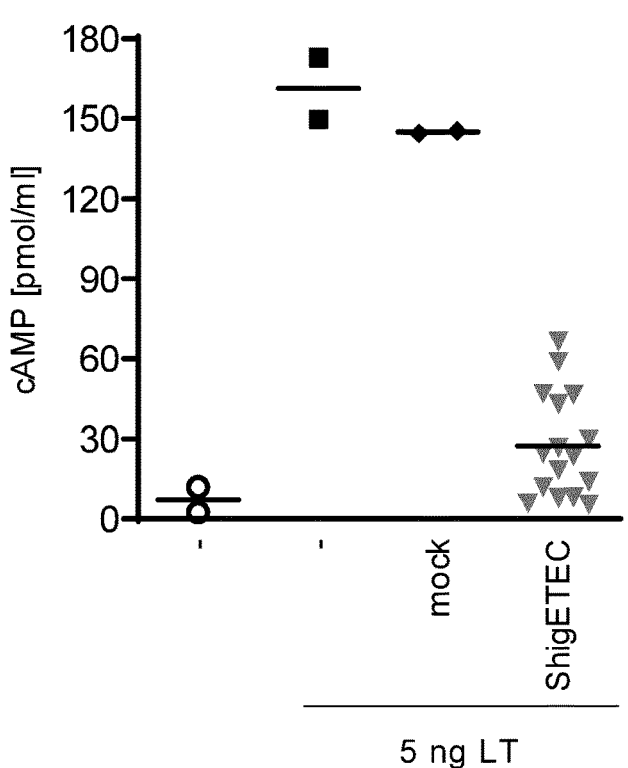

B

Fig. 7

SEQ ID NO:1: STm amino acid sequence

NSSNYCCELCCXXACTGCY wherein

X at position 12 is S, N, K or R, and/or

X at position 13 is P, G, L or F,

SEQ ID NO:2: wild-type ST sequence

NSSNYCCELCCNPACTGCY

SEQ ID NO:3: LTB amino acid sequence

MNKVKCYVLFTALPSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMEN

SEQ ID NO:4: NSSNYCCELCCSPACTGCY

SEQ ID NO:5: NSSNYCCELCCKPACTGCY

SEQ ID NO:6: NSSNYCCELCCRPACTGCY

SEQ ID NO:7: NSSNYCCELCCNGACTGCY

SEQ ID NO:8: NSSNYCCELCCNLACTGCY

SEQ ID NO:9: NSSNYCCELCCNFACTGCY

Fig. 7 (continued)

SEQ ID NO:10: LTB-STm (without a linker)

MNKVKCYVLFTALPSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMENNSSNYCCELCCXXACTGCY
     wherein
     X at position 136 is S, N, K or R, and/or
     X at position 137 is P, G, L or F,
     Preferably wherein SEQ ID NO:10 does not comprise:
NSSNYCCELCCNPACTGCY (SEQ ID NO:2).

SEQ ID NO:11: LTB ST(N12S) without a linker:

MNKVKCYVLFTALPSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMENNSSNYCCELCCSPACTGCY-

SEQ ID NO:12: LTB ST(N12S) including a linker GPGP (SEQ ID NO:20, underlined):

MNKVKCYVLFTALPSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMEN<u>GPGP</u>NSSNYCCELCCSPACTGCY

SEQ ID NO:13: nucleotide sequence encoding SEQ ID NO:12:

LTB (in bold); <u>ST(N12S) (underlined)</u>, linker sequence (no emphasis added)

**Atgaataaagtaaaatgttatgttttatttacggcgttaccatcctctctatgtgcatacggagctccccagtctatt
acagaactatgttcggaatatcgcaacacacaaatatatacgataaatgacaagatactatcatatacggaatc
gatggcaggcaaaagagaaatggttatcattacatttaagagcggcgcaacatttcaggtcgaagtcccgggc
agtcaacatatagactcccaaaaaaaagccattgaaaggatgaaggacacattaagaatcacatatctgaccg
agaccaaaattgataaattatgtgtatggaataataaaacccccaattcaattgcggcaatcagtatggaaaac**g
ggccggggccc<u>aattcttctaactactgctgtgaactttgttgttctcctgcctgtacaggatgttactag</u>

SEQ ID NO:14: nucleotide sequence encoding SEQ ID NO:11:

LTB (in bold); <u>ST(N12S) (underlined)</u>

**atgaataaagtaaaatgttatgttttatttacggcgttaccatcctctctatgtgcatacggagctccccagtctatta
cagaactatgttcggaatatcgcaacacacaaatatatacgataaatgacaagatactatcatatacggaatcg
atggcaggcaaaagagaaatggttatcattacatttaagagcggcgcaacatttcaggtcgaagtcccgggca
gtcaacatatagactcccaaaaaaaagccattgaaaggatgaaggacacattaagaatcacatatctgaccga
gaccaaaattgataaattatgtgtatggaataataaaacccccaattcaattgcggcaatcagtatggaaaac**<u>aa
ttcttctaactactgctgtgaactttgttgttctcctgcctgtacaggatgttactag</u>

Fig. 7 (continued)

SEQ ID NO:15: Promotor (249bp) originating from *E. coli*:

gctgccgtggttcaagtcgcgactaataaaaataatcaggttgccatgattcaatgtacacctttctcacattcgtctccggc
atgaaaacgatgcactctttctttatcgctttcactacacattttatcctcgcatggatgttttataaaaaacatgattgacatcat
gttgcatataggttaaacaaaacaagtggcgttatctttttccggattgtcttcttgtatgatatataagttttcctcg SEQ ID NO:16: Terminator after the first LTB-ST(N12S)

tttgctttaaaagcatgtctaatgctaggaacctatataacaactactgtacttatactaatgagccttatgctgcatttgaact
aaagcggccgccagatcttccggatggctcgag SEQ ID NO:17: Terminator after the second LTB-ST(N12S)

tttgctttaaaagcatgtctaatgaatccgctcgag

SEQ ID NO:18: Terminator after the third LTB-ST(N12S)

tttgctttaaaagcatgtctaatgctaggaacctatataacaactactgtacttatactaatgagccttatgctgcatttgaaaa
ggcggtagaggatgcaat

Fig. 7 (continued)

SEQ ID NO:19: *infA*-3x[LTB-ST(N12S)] insertion into the invasion plasmid of ShigETEC, LTA promotor LTB ST(N12S), * Insertion sites gtcgcaaaacatgtcattcaggttcatctcaccaataaggatatgagtgaagtggaggataagtgagtctgctgtcagagt
tttctggtgtatgtcagtaa*gggtaccacggtgcttgttttcaccacaagaatgaatgttttcggcacatttctccccagagtg
ttataattgcggtcgcagagttggttacgctcattaccccgctgccgataaggaattttttcgcgtcaggtaacgcccatcgttt
atctcaccgctcccttatacgttgcgcttttggtgcggcttagccgtgtgtttttcggagtaatgtgccgaacctgtttgttgcgatt
tagcgcgcaaatctttacttatttacagaacttcggcattatcttgccggttcaaattacggtagtgataccccagaggattag
*atggccaaagaagacaatattgaaatgcaaggtaccgttcttgaaacgttgcctaataccatgttccgcgtagagttaga*
*aaacggtcacgtggttactgcacacatctccggtaaaatgcgcaaaaactacatccgcatcctgacgggcgacaaagt*
*gactgttgaactgaccccgtacgacctgagcaaaggccgcattgtcttccgtagtcgctgatt*gttttaccgcctgatgggc
gaagagaaagaacgagtaaaaggtcggtttaaccggcctttttattttgtgatatgtatgaagtactttggaagtataagtcc
ataacttgtctcgatgtaggcggccgc<u>gctgccgtggttcaagtcgcgactaataaaaataatcaggttgccatgattcaat</u>
<u>gtacacctttctcacattcgtctccggcatgaaaacgatgcactctttctttatcgctttcactacacattttatcctcgcatggat</u>
<u>gtttttataaaaaacatgattgacatcatgttgcatataggttaaacaaaacaagtggcgttatctttttccggattgtcttcttgt</u>
<u>atgatatataagttttcctcg</u>atgaataaagtaaaatgttatgttttatttacggcgttaccatcctctctatgtgcatacg
gagctccccagtctattacagaactatgttcggaatatcgcaacacacaaatatatacgataaatgacaagata
ctatcatatacggaatcgatggcaggcaaaagagaaatggttatcattacatttaagagcggcgcaacatttca
ggtcgaagtcccgggcagtcaacatatagactcccaaaaaaaagccattgaaaggatgaaggacacattaa
gaatcacatatctgaccgagaccaaaattgataaattatgtgtatggaataataaaacccccaattcaattgcgg
caatcagtatggaaaacgggccggggccc<u>aattcttctaactactgctgtgaactttgttgttctcctgcctgtacaggatg</u>
<u>ttactag</u>tttgctttaaaagcatgtctaatgctaggaacctatataacaactactgtacttatactaatgagccttatgctgcatt
tgaactaaagcggccgccagatcttccggatggctcgag<u>gctgccgtggttcaagtcgcgactaataaaaataatcagg</u>
<u>ttgccatgattcaatgtacacctttctcacattcgtctccggcatgaaaacgatgcactctttctttatcgctttcactacacatttt</u>
<u>atcctcgcatggatgtttttataaaaaacatgattgacatcatgttgcatataggttaaacaaaacaagtggcgttatctttttcc</u>
<u>ggattgtcttcttgtatgatatataagttttcctcg</u>atgaataaagtaaaatgttatgttttatttacggcgttaccatcctctc
tatgtgcatacggagctccccagtctattacagaactatgttcggaatatcgcaacacacaaatatatacgataa
atgacaagatactatcatatacggaatcgatggcaggcaaaagagaaatggttatcattacatttaagagcggc
gcaacatttcaggtcgaagtcccgggcagtcaacatatagactcccaaaaaaaagccattgaaaggatgaag
gacacattaagaatcacatatctgaccgagaccaaaattgataaattatgtgtatggaataataaaaccccccaat
tcaattgcggcaatcagtatggaaaacgggccggggccc<u>aattcttctaactactgctgtgaacttgttgttctcctgcc</u>
<u>tgtacaggatgttactag</u>tttgctttaaaagcatgtctaatgaatccgctcgag<u>gctgccgtggttcaagtcgcgactaataa</u>
<u>aaataatcaggttgccatgattcaatgtacacctttctcacattcgtctccggcatgaaaacgatgcactctttctttatcgcttt</u>
<u>cactacacattttatcctcgcatggatgtttttataaaaaacatgattgacatcatgttgcatataggttaaacaaaacaagtg</u>
<u>gcgttatctttttccggattgtcttcttgtatgatatataagttttcctcg</u>atgaataaagtaaaatgttatgttttatttacggcg
ttaccatcctctctatgtgcatacggagctccccagtctattacagaactatgttcggaatatcgcaacacacaaa
tatatacgataaatgacaagatactatcatatacggaatcgatggcaggcaaaagagaaatggttatcattacat
ttaagagcggcgcaacatttcaggtcgaagtcccgggcagtcaacatatagactcccaaaaaaaagccattg
aaaggatgaaggacacattaagaatcacatatctgaccgagaccaaaattgataaattatgtgtatggaataata
aaaccccccaattcaattgcggcaatcagtatggaaaacgggccggggccc<u>aattcttctaactactgctgtgaacttt</u>
<u>gttgttctcctgcctgtacaggatgttactag</u>tttgctttaaaagcatgtctaatgctaggaacctatataacaactactgtactt
atactaatgagccttatgctgcatttgaaaaggcggtagaggatgcaatgtttaaacgtgtaggctggagctgcttcgaag
ttcctatactttctagagaataggaacttcggaataggaactaaggaggatattcatatg*gatgaatgttcaggctatcttta
tcttgatggtggttcagctgtttggtaaagaaatcgctgtaacaatagaagaactgcaggcagtactggtcccacatcgttt
gctcagtcaactggtgaagttccgtagcgcgtaaattaatgctttgcatgaaacgttactggagtggatgaaag SEQ ID NO:20: linker: GPGP Fig. 8
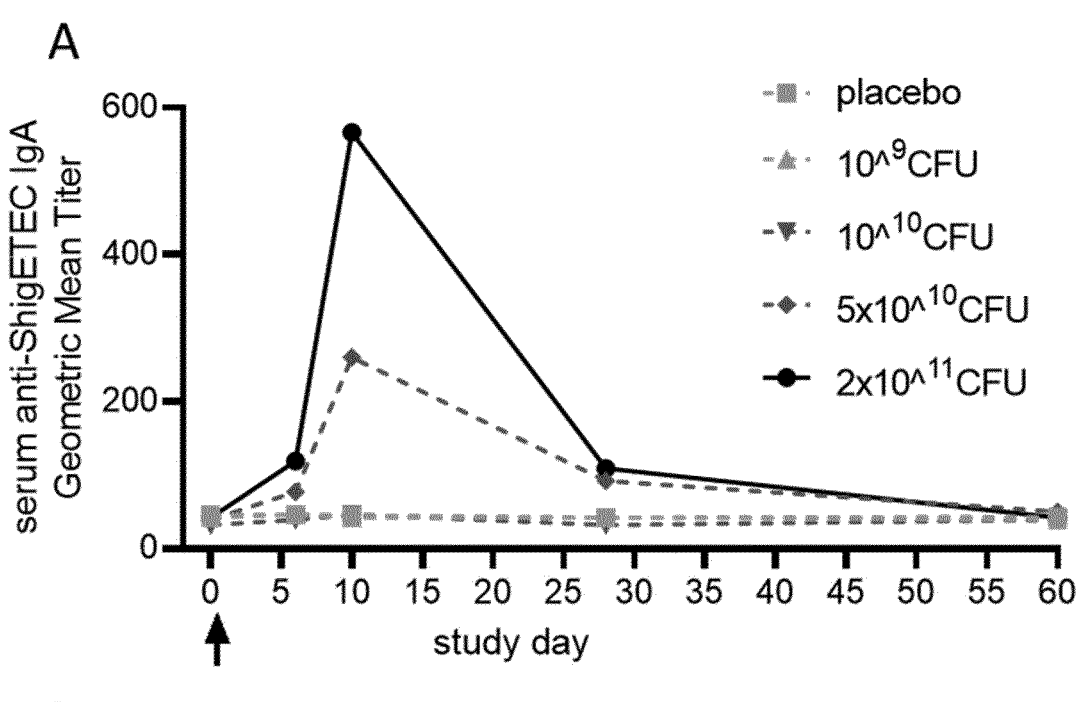
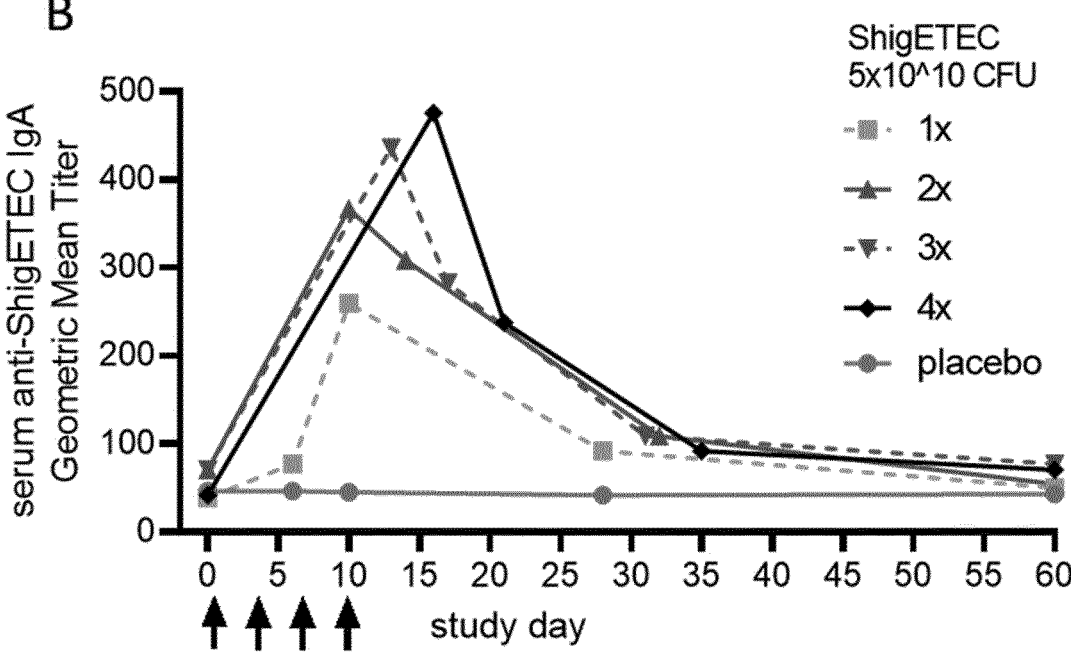

HIGH DOSE SHIGELLA VACCINE PREPARATION

This application is a National Phase Application under 35 U.S.C § 371 of International Application PCT/EP2021/076378, filed Sep. 24, 2021, which claims the benefit of European Patent Application No. 20201844.6, filed Oct. 14, 2020, the entireties of which are incorporated herein by reference.

Pursuant to 37 C.F.R. 1.821 (c), a sequence listing is submitted herewith as an ASCII compliant text file named "REDL.P0006US_ST25.txt", created on Mar. 23, 2022, and having a size of ~16 kilobytes. The content of the aforementioned file is hereby incorporated by reference in its entirety.

FIELD OF THE INVENTION

The present invention relates to novel attenuated *Shigella* vaccine in a high dose preparation, which is non-reactogenic through specific chromosomal and invasion plasmid mutations.

BACKGROUND OF THE INVENTION

Diarrheal diseases represent a significant medical burden worldwide. Shigellae and entrotoxigenic *Escherichia coli* (ETEC) remain the two leading bacterial causes of diarrheal manifestations in children under 5 years of age in endemic regions, travelers from high to low and middle income countries, as well as military personnel deployed to endemic regions. Current reports indicate that the 950 million global yearly diarrheal episodes lead to 1.3 million deaths out of which 500 000 affect children under 5 years of age. Shigellae alone contribute with 125 million episodes per year and the 165 000 cases that occur with children under 5 years of age result in 55 000 deaths. ETEC extends this rate by an estimated additional 20 000 fatalities.

Infections by members of the *Shigella* genus lead to moderate to severe intestinal syndrome called bacillary dysentery or shigellosis. Natural immunity is serotype specific and protection usually develops against the encountered serotype and not against the other approx. 50 serotypes of the four *Shigella* species. The natural response is predominantly directed against the immunodominant O-antigen moiety of the bacterial lipopolysaccharide (LPS) structure. An ideal *Shigella* vaccine, nevertheless, should elicit protection against all prevalent serotypes. Another caveat in *Shigella* vaccine development has been the optimal balance between immunogenicity and safety (Levine, Nat Rev Microbiol 2007, 5: 540-553).

ETEC is a mucosal enteric pathogen that has overlapping endemicity with *Shigella*, and infection occurs via the fecal-oral route, such as in case of shigellosis, in areas with low sanitary infrastructure. This pathogen exerts its pathogenicity via two major endotoxins, the heat-stable (ST) and heat-labile (LT) toxins. ST is a 19 amino acid peptide with high toxicity and poor immunogenicity. LT is a complex macromolecule, consisting of one LT-A subunit and 5 LT-B subunits. The LT holotoxin is closely related both structurally and functionally to cholera toxin (CT). ETEC strains may express either LT or ST, but often both. Therefore, a viable vaccine should target both LT and ST. Despite multiple attempts, it has been difficult to generate high titer neutralizing antibodies against ETEC toxins. An oral immunization route would be amenable to deliver sufficiently detoxified, yet ideally immunogenic antigens, a task that has not yet been successfully addressed (Buergeois, et al. 2016, Vaccine, 34: 2887-2894; Tribble, 2017; J Travel Med, 1: S6-S12). Moreover, as for *Shigella*, growing antibiotic resistance has been reported for ETEC as well.

Kotloff et al. (INFECTION AND IMMUNITY 2000, 68(3):1034-1039) describe a live attenuated *Shigella flexneri* 2a vaccine candidate with specific deletion mutations in virG, sen, set, and guaBA. CVD 1207 expresses type-specific O-polysaccharide and invades epithelial cells. It was found well-tolerated at inocula up to 10E8 CFU. However, at a dose of 10E9 CFU, mild diarrhea and a single episode of emesis was experienced. At a dose of 10E10 CFU a subject experienced watery diarrhea and emesis.

Kotloff et al. (The Journal of Infectious Diseases 2004; 190:1745-54) describe vaccine strains (1) ΔguaBA *Shigella flexneri* 2a, which harbors deletions in the guanine nucleotide synthesis pathway (CVD 1204); and (2) additional attenuation conferred by deletions in set and sen genes encoding *Shigella* enterotoxins (ShETs) 1 and 2, respectively (CVD 1208); and the relative immunogenicity of these constructs. It was observed that Δset and Δsen does not affect invasiveness in HeLa cells. It was demonstrated that CVD 1204 and CVD 1208, which express invasion plasmid antigens (IPAs) in their native form, stimulate antibody responses to highly purified recombinant IPAB, -C, and -D and that the response to IPAB was immunodominant. A single oral dose of CVD 1204 and CVD 1208 (10E7, 10E8, or 10E9 CFU), resulted in a few mild to moderate side effects.

Kotloff et al. (Human Vaccines 2007, 3(6):268-275) describe that *Shigella flexneri* 2a deleted in guaBA, sen and set (strain CVD 1208) was well-tolerated and immunogenic after a single oral dose of 10E8 or 10E9 CFU, though mild diarrhea or several hours of low-grade fever was observed in 14% of subjects who ingested either 10E8 or 10E9 CFU.

Noriega et al. (Infection and Immunity 67(2): 782-788, 1999) described a strategy for cross-protection against 14 *Shigella flexneri* serotypes, involving the use of the two serotypes 2a and 3a. The attenuated strains described are *S. flexneri* 2a strain CVD1207 (ΔguaB-A Δset1 Δsen) and *S. flexneri* 3a strain CVD 1211 (ΔguaB-A ΔvirG Δsen).

Fiorentino et al. (PLoS ONE 2014, 9(1): e85211) describe that wild-type *Shigella* infection causes a severe alteration of the barrier function of a small intestinal cell monolayer (a proxy for mucosa) and might contribute (along with enterotoxins) to the induction of watery diarrhea. Vaccine candidates, which are depleted of the major enterotoxins (ShET1/2 and stx), suggest that the increased paracellular permeability observed in Caco2 monolayers following exposure at the highest bacterial inoculum, might be attributed to a specific response of the host to infection rather than to bacterial toxins. The fact that attenuated *Shigella* strains induce a remarkable immune reaction, shows that the host immune response is not only independent of the functional impairment of the epithelial barrier but also of the bacteria main effector enterotoxic activities (ShET 1/2 and stx).

WO2014037440A2 discloses a live attenuated *Shigella* vaccine strain generated with specific targeted mutations in order to induce serotype independent cross-protection and express heterologous (non-*Shigella*) antigens. An exemplary *Shigella flexneri* 2a 2457T strain comprises a ΔrfbF mutation thereby obtaining a rough phenotype, and a ΔipaBC mutation to render the strain non-invasive.

Ranallo et al. (Vaccine 2012, 30:5159-5171) describe *Shigella flexneri* 2a strains WRSf2G12 and WRSf2G15, two live attenuated vaccine candidates that are proven to be invasive in an epithelial cell invasion assay using HeLa cells. Both strains lack virG and are invasive as determined by an epithelial cell invasion assay, but do not spread intercellularly, a feature that is determined by the Sereny test.

Medeiros et al. (npj Vaccines 2020, Article number 30) describe a bivalent (combined) vaccine conferring immunogenicity and protection against *S. flexneri* and enterotoxigenic *E. coli* infections in mice.

SUMMARY OF THE INVENTION

It is the objective of the present invention to provide *Shigella* vaccines, in particular for the prevention of diarrheal diseases, that are highly immunogenic with an improved safety profile.

The objective is solved by the subject of the present claims and as further described herein.

The invention provides for a *Shigella* vaccine preparation comprising 10E8-10E12 CFU of a live, genetically attenuated *Shigella flexneri* strain that comprises a chromosomal deletion of setBA and which is non-invasive as determined by the Sereny test and by an in vitro invasion assay using HeLa cells, or a human epithelial cell, such as in a human epithelial cell invasion test using e.g., HeLa cells. Specifically, the strain comprises an endogenous invasion plasmid that is genetically engineered to incorporate a heterologous expression construct expressing a pathogen-specific antigen.

Specifically, the preparation comprises a dose which is at least 10E8, 5×10E8, 10E9, 5×10E9, 10E10, 5×10E10, 10E11, 5×10E11, or 10E12 CFU, preferably up to a maximum tolerable dose, such as e.g., any one of 5×10E10, 6×10E10, 7×10E10, 8×10E10, 9×10E10, 1×10E11, 2×10E11, 3×10E11, 4×10E11, 5×10E11, 6×10E11, 7×10E11, 8×10E11, 9×10E11, or 1×10E12.

Specifically, the *Shigella* vaccine preparation comprises the CFU amount in a predefined volume, such as per at least any one of 100 μL, 1 mL, 5 mL, 10 mL, 15 mL, 20 mL, 25 mL, 30 mL, 35 mL, 40 mL, 45 mL, or 50 mL. Any volume as conveniently used to administer the vaccine preparation by a specific route (such as oral, nasal, or mucosal) may be used.

According to a specific aspect, the *Shigella flexneri* strain is a *Shigella flexneri* 2a strain or a *Shigella flexneri* 2b strain. Specifically, the strain is the *Shigella flexneri* 2a strain 2457T.

Specifically, the strain comprises a deletion of the set gene(s) that are endogenous to the wild-type *Shigella flexneri* strain, in particular a Δset or ΔsetBA mutation.

Specifically, the strain comprises an endogenous invasion plasmid that carries the endogenous sen gene.

According to a specific aspect, the *Shigella flexneri* strain comprises an endogenous invasion plasmid which comprises (or which encodes) an inactivated Type III Secretion System (T3SS) through genetic modification of the invasion plasmid, preferably wherein the genetic modification comprises a deletion or inactivation of one or more genes expressing components of the T3SS.

Specifically, the genetic modification of the invasion plasmid comprises a deletion or inactivation of any one of genes in the invasion locus.

Specifically said deletion or inactivation is of one or more of the genes in the invasion locus, in particular within the ipa operon (such as selected from the group consisting of IpaB, IpaC, IpaA, and IpaD), or within the mxi/spa operon, or one or more of the genes which are regulators of the T3SS (such as selected from the group consisting of VirB and VirF).

Specific gene products (or genes) referred to herein are the following:

Ipa Operon:

IpaJ (ipaJ), VirB (virB), Acp (acp), IpaA (ipaA), IpaD (ipaD), IpaC (ipaC), IpaB (ipaB), IpgC (ipgC), IpgB1 (ipgB1), IpgA (ipgA), IcsB (icsB), Mxi/Spa Operon:

IpgD (ipgD), IpgE (ipgE), IpgF (ipgF), MxiG (mxiG), MxiH (mxiH), MxiI (mxiI), MxiJ (mxiJ), MxiK (mxiK), MxiN (mxiN), MxiL (mxiL), MxiM (mxiM), MxiE (mxiE), MxiD (mxiD), MxiC (mxiC), MxiA (mxiA), Spa15 (spa15), Spa47 (spa47), Spa13 (spa13), Spa32 (spa32), Spa33 (spa33), Spa24 (spa24), Spa9 (spa9), Spa29 (spa29), Spa40 (spa40), ORF131a (ORF131a), and ORF131b (ORF131b).

Specifically, the strain is non-invasive through a mutation of the invasion plasmid to delete one or more genes expressing components of the T3SS, such as genes carried on the ipa or mxi/spa operons, or regulators of the T3SS.

According to a specific example, the strain comprises a deletion of the ipaB and/or ipaC and/or other ipa genes.

Specifically, the non-invasive phenotype is characterized by the lack of invasion to epithelial cells and therefore not being taken up by the epithelial cells. In addition, the vaccine strain bacteria are unable to spread within or between infected cells, thus, unable to spread intercellularly and intracellularly. Therefore, the strain is truly non-invasive.

Specifically, the non-invasive phenotype is determined by an in vitro epithelial cell invasion test using HeLa cells, as further described herein.

Specifically, the non-invasive phenotype is determined by a standard Sereny test for in vivo determination of bacterial invasiveness, as measured in guinea pigs. An exemplary test is further described herein.

According to a specific aspect, the *Shigella flexneri* strain comprises a mutation on the endogenous invasion plasmid to incorporate a heterologous expression construct, specifically a genetic construct expressing one or more pathogen-specific antigen(s), in particular wherein the pathogen-specific antigen(s) are heterologous to the host cell.

Specifically, the heterologous expression construct comprises a nucleotide sequence encoding an antigen originating from a pathogen.

Specifically, the antigen is selected from the group consisting of a bacterial antigen, a viral antigen, a fungal antigen, and a parasitic antigen.

Specifically, the antigen is a protective antigen originating from a pathogen, e.g. selected from the group consisting of a) a bacterial antigen preferably a toxin or colonization factor, b) —a viral antigen, preferably from a pathogen causing enteral or mucosal infections, c) —a fungal antigen, preferably from a pathogen causing enteral or mucosal infections, and d) a parasitic antigen, preferably from a pathogen causing enteral infections.

Specifically, the bacterial antigen is originating from enteropathogenic bacteria, preferably selected from the group consisting of a. *E. coli* antigens, in particular an enterotoxin selected from the group consisting of LTB, mutated LTA and ST of ETEC, fragments, subunits, or fusions thereof, antigens from enteroaggregative *E. coli* (EAEC), or Shiga-like toxin 1 or 2

5 b. *Campylobacter jejuni* antigens, c. *Clostridium difficile* antigens, specifically toxins A and B d. *Vibrio cholera* antigens, specifically the CTA or CTB antigen, and e. mutants or fusion proteins of a), b) c) or d).

According to a specific aspect, the antigen consists of a fusion of the B subunit of heat labile toxin (LTB) and a mutated heat stable toxin (STm) of enterotoxigenic *Escherichia coli* (ETEC).

Specifically, the STm comprises or consists of SEQ ID NO:1, preferably excluding the wild-type sequence of the heat stable toxin ST (SEQ ID NO:2).

In particular, said ETEC antigen is a fusion protein of the B subunit of LT and mutant ST (with or without a linker between the LTB and ST), preferably a fusion protein LTB-STm comprising or consisting of an LTB sequence (such as SEQ ID NO:3) and an STm sequence, such as any one of SEQ ID NO:1, 4, 5, 6, 7, 8, or 9, for example which comprises with ST mutations at position 13 and/or 12, such as N12S, N12R or N12K at position 12; and/or P13F or P13G at position 13.

According to a specific embodiment, STm comprises or consists of

```
                                    SEQ ID NO: 1
        NSSNYCCELCCXXACTGCY
``` wherein

X at position 12 is S, N, K or R, and/or

X at position 13 is P, G, L or F,

Preferably wherein the STm sequence is not the wild-type ST sequence consisting of:

```
                                  (SEQ ID NO: 2)
        NSSNYCCELCCNPACTGCY.
```

According to a specific aspect, a) the LTB comprises or consists of an amino acid sequence at least 90%, 95%, 98%, or 100% identical to SEQ ID NO:3; and b) the STm comprises or consists of any one of SEQ ID NO:1, 4, 5, 6, 7, 8, or 9.

According to a specific example, the LTB-STm comprises or consists of SEQ ID NO:10, 11 or 12, optionally wherein the LTB-STm sequence comprises a linker between the LTB and the STm sequence.

According to a specific example, the LTB-STm sequence that comprises a linker between the LTB and the STm sequence comprises or consists of SEQ ID NO:12.

The linker may be a peptide consisting of a sequence of at least 3, 4, 5, or 6, up to e.g. 30, 25, 20, 15, or 10 amino acids, preferably consisting of glycine and/or proline and/or serine.

Exemplary LTB-STm comprise the LTB and STm, such as in SEQ ID NO:11, with or without a linker, such as a linker comprising or consisting of e.g. GPGP (SEQ ID NO:20).

According to a specific aspect, the nucleotide sequence encoding LTB-STm is at least 90%, 95%, 98% or 100% identical to SEQ ID NO:13 or 14.

Specifically, the viral antigen is originating from diarrheal viruses, preferably selected from the group consisting of rotaviruses and Norwalk virus (caliciviruses).

Specifically, the parasite antigen is originating from diarrhea-causing protozoa, preferably selected from the group consisting of *Giardia lamblia, Cryptosporidium* species and *Entameba histolytica.*

Specifically, the fungal antigen is originating from diarrhea-causing fungi, preferably selected from the group consisting of *Blastomyces dermatiditis* and *Histoplasma* spp.

According to a specific aspect, the heterologous expression construct comprises a nucleotide sequence encoding at least two or at least three of said antigens, such as in the form of a tandem sequence (understood as a fusion sequence), wherein one coding sequence is fused to another coding sequence.

Specifically, a tandem sequence comprises a promoter before (upstream) each of the antigen coding sequences. Specifically, the coding sequences end with a stop codon. Specific terminator sequences can be used following (downstream) each of the antigen coding sequences.

Exemplary tandem constructs comprise one or more copies of the promoter comprising the upstream region of the MBA operon of ETEC, such as a promoter comprising or consisting of SEQ ID NO:15.

Specifically, identical or different promoter can be used upstream of each antigen coding sequence to control expression of the antigens.

Specifically, identical or different terminator sequences can be used. Specific examples of terminator sequences comprise or consist of any of SEQ ID NO:16, 17, or 18, or any other suitable sequences comprising a translational termination sequence.

According to a specific example, the tandem nucleotide sequence comprises two copies or three copies of an antigen-coding sequence, to express two and three copies of an antigen, such as tandem repeats of nucleic acid sequences, e.g., wherein at least two or three copies of an antigen are expressed from such tandem repeats.

Specific examples tandem nucleotide sequence comprise a doublet or triplet of LTB-STm coding sequences, such as comprising at least two nucleic acid sequences encoding at least two of the antigens comprising or consisting of SEQ ID NO:10, with or without a linker between the LTB and ST sequence, e.g., comprising at least one, two or three of nucleic acid sequences encoding SEQ ID NO:11 or SEQ ID NO:12, such as at least one, two or three of nucleic acid sequences comprising or consisting of SEQ ID NO:13 (encoding SEQ ID NO:12) or SEQ ID NO:14 (encoding SEQ ID NO:12).

According to a specific aspect, the *Shigella flexneri* strain comprises an endogenous invasion plasmid that comprises a genetic modification to incorporate a *Shigella* essential gene, preferably selected from the group consisting of infA, ppa, accD, acpS, dapE, era, frr, ftsI, ftsL, ftsN, ftsZ, lgt, lpxC, msbA, murA, murI, nadE, parC, proS, pyrB, rpsB, trmA, rho and rhoL.

Specifically, the *Shigella* essential gene is inserted into an expression construct integrated into the invasion plasmid. Such expression construct comprises a promoter operably linked to the *Shigella* essential gene.

Specifically, the *Shigella* essential gene incorporated into the invasion plasmid is heterologous to the invasion plasmid. Yet, it can be a *Shigella* endogenous gene, such as a gene naturally occurring in *Shigella* but heterologous to the invasion plasmid, or a chromosomal gene.

Specifically, the original allele of the chromosomal *Shigella* essential gene is deleted in the *Shigella* vaccine strain.

According to a specific aspect, the *Shigella* essential gene is inserted en bloc with a heterologous expression construct expressing a pathogen-specific antigen.

According to a specific aspect, the *Shigella flexneri* strain is of the rough phenotype through a chromosomal deletion of one or more endogenous genes reducing LPS-O-antigens as compared to such strain without the chromosomal deletion.

Specifically, the endogenous genes are selected from the group consisting of genes of the rfb/wbb gene cluster, genes of the rfa/waa gene cluster, wzx, wzy/rfc, and rfaH.

Specifically, the vaccine is attenuated by mutagenesis of one or more genes involved in the LPS synthesis, transport and expression.

According to a specific embodiment, said deletion is of one or more of the rfb F, D, C, E, J and/or I genes, or a deletion of a part thereof, or corresponding genes in various *Shigella* serotypes.

Specifically, the deletion of one or more of the endogenous genes results in reducing the respective LPS-O-antigen expression, e.g., by at least 90%.

According to a specific aspect, there is provided a *Shigella* strain, which is a *S. flexneri* 2a strain, such as *S. flexneri* 2a 2457T, with a deletion of the rfbF and a deletion of one or both of the ipaB and ipaC genes, or a deletion of essential parts thereof. Specifically, such *Shigella* strain may further comprise a deletion of an essential chromosomal gene and an insertion of said gene into the invasion plasmid. Specifically, said *Shigella* strain comprises a recombinant invasion plasmid incorporating at least one heterologous expression construct expressing a gene encoding a heterologous antigen.

According to a specific aspect, the invention provides for the construction of a live, attenuated, non-invasive *Shigella* vaccine strain that does not express the O-antigen component of LPS and elicit serotype-independent protection against Shigellae. According to a specific example, a heterologous LT-ST fusion protein is expressed by the vaccine strain in order to address ETEC for a broader coverage of diarrhoeal pathogens.

According to a specific example, the *Shigella flexneri* strain is characterized by the genotype *Shigella flexneri* 2457TΔrfbFΔipaBCAinfAΔsetBA::infA-3x[LTB-ST (N12S)].

The invention further provides for a pharmaceutical preparation comprising the *Shigella* vaccine preparation described herein, providing a specific dose, in particular for a single use.

Specifically, the dose is an effective dose to trigger immune response, e.g. upon one or more (such as repeated) administrations.

Specifically, the preparation is provided in a formulation that is suitable to be administered to a subject in need of such vaccine by a one-time (or single) administration. Specifically, the vaccine can be administered to the subject in an effective amount employing a prime-boost strategy.

The preparation may comprise a pharmaceutically acceptable carrier, e.g. in an immunogenic formulation, and optionally may or may not include an adjuvant.

The invention further provides a kit of components for preparing pharmaceutical preparation or vaccine described herein, e.g. a pharmaceutical kit comprising one or more containers filled with one or more kit components, such as the *Shigella* strain and pharmaceutically acceptable carriers. The kit can be used to prepare a vaccine in vitro, before administering to a subject. In a particular embodiment, the kit further comprises instructions for using the kit components.

According to a specific aspect, the *Shigella flexneri* strain is provided in a pharmaceutical preparation comprising an oral (including peroral) or mucosal formulation, preferably as a liquid, powder, or tablet.

Specifically, treatment comprises administration of the vaccine described herein in a respective formulation. Specifically, the vaccine is administered to a subject by oral, sublingual, intranasal, or intragastric administration.

According to a specific aspect, the invention further provides for the medical use of the *Shigella* vaccine preparation described herein. Specifically, the medical use involves an immunotherapy, in particular immunoprophylaxis, such as an active immunotherapy. Specific immunotherapies provide for the treatment of a subject afflicted with, or at risk of contracting or suffering a disease or recurrence of a disease, by a method comprising inducing, enhancing, suppressing or otherwise modifying an immune response.

The invention further provides for the use of the vaccine and respective preparation in the treatment of a subject to induce an immune response against an infection by *Shigella*, or an immune response against a heterologous antigen expressed by the *Shigella flexneri* strain.

Therefore, the invention specifically provides for a method of treating a subject in need of prophylactic treatment by administering an effective amount of the vaccine, e.g. to prevent a *Shigella* infection or the outbreak of a *Shigella* disease, and optionally infection by a target pathogen (or the respective pathogen-specific disease), for which a heterologous antigen expressed by said *Shigella* strain is specific to.

Specifically, the *Shigella flexneri* strain expresses an ETEC antigen as a heterologous antigen, and the immunoprophylaxis is against infectious disease which is caused by ETEC as a target pathogen.

According to the invention, there is further provided a method of preventing infectious disease in a subject, by vaccination and immunizing a subject in need thereof.

Specifically, the infectious disease is a disease or disease condition caused by a target *Shigella* or target pathogen, in particular a target pathogen which is heterologous to *Shigella*. According to a specific aspect, the vaccine is provided for use in the prophylaxis or immunoprophylaxis of a subject to prevent infectious diseases, in particular enteral disease, such as diarrheal disease. Specifically, the disease is selected from the group consisting of Shigellosis, dysentery and diarrhea.

According to the invention, there is further provided a method of preventing infectious disease in a subject, in particular enteral disease, specifically by administering an effective amount of the vaccine preparation described herein.

Specifically, said enteral disease is caused by any *Shigella* serotype or species.

A specific embodiment refers to a vaccine, wherein the vaccine is a polyvalent vaccine using a strain expressing one or more of heterologous antigens and *Shigella* antigens.

Specifically, the immune response is protective against one or more of *S. flexneri* (any or all serotypes of *S. flexneri*), *S. sonnei, S. dysentheriae* (any or all serotypes of *S. dysentheriae*), and *S. boydii* (any or all serotypes of *S. boydii*).

Specifically, the immune response is cross-protective targeting one or more of *S. flexneri* (any or all serotypes of *S.*

*flexneri*), *S. sonnei*, *S. dysentheriae* (any or all serotypes of *S. dysentheriae*), and *S. boydii* (any or all serotypes of *S. boydii*).

Specifically, the vaccine elicits serotype-independent protection against Shigellae in the mouse lethal lung challenge model.

According to a specific aspect, the *Shigella flexneri* strain comprises a mutation on the endogenous invasion plasmid to incorporate a heterologous expression construct expressing a pathogen-specific antigen, for use in treatment of a subject to induce an immune response against the pathogen for which the antigen is specific to.

According to a specific aspect, the treatment induces serum, mucosal and/or fecal immune response, preferably inducing specific IgA, IgG and/or IgM antibodies.

According to a specific aspect, the vaccine preparation is tolerable and non-reactogenic in a subject, e.g. determined by the absence of nausea or vomiting, diarrhea, abdominal pain, loss of appetite, headache, fatigue or myalgia.

According to a further aspect, the invention provides for a method of producing the vaccine preparation described herein.

Specifically, the method comprises the following steps:

a) providing a parental *Shigella flexneri* strain;

b) attenuating the strain by i. a chromosomal deletion of endogenous set and to render it non-invasive;

ii. optionally engineering the strain to reduce LPS O-antigens, preferably to obtain a rough LPS phenotype; and iii. optionally engineering the strain to incorporate a heterologous expression construct into the endogenous invasion plasmid, which heterologous expression construct expresses a pathogen-specific antigen; and iv. optionally engineering the strain to incorporate a *Shigella* essential gene into the endogenous invasion plasmid, preferably wherein the *Shigella* essential gene has been deleted from the *Shigella* chromosome;

c) culturing the strain and preparing a vaccine formulation comprising a predefined amount of CFU.

Specifically, the vaccine preparation is provided in the lyophilized or frozen form.

Specific formulations comprise a buffer such as a PBS buffer, optionally containing PEG, such as 10% PEG-6000. According to a specific example, the vaccine preparation is formulated as a frozen concentrate of live bacteria, provided for oral delivery upon thawing an optionally diluting.

FIGURES

Figure 1:
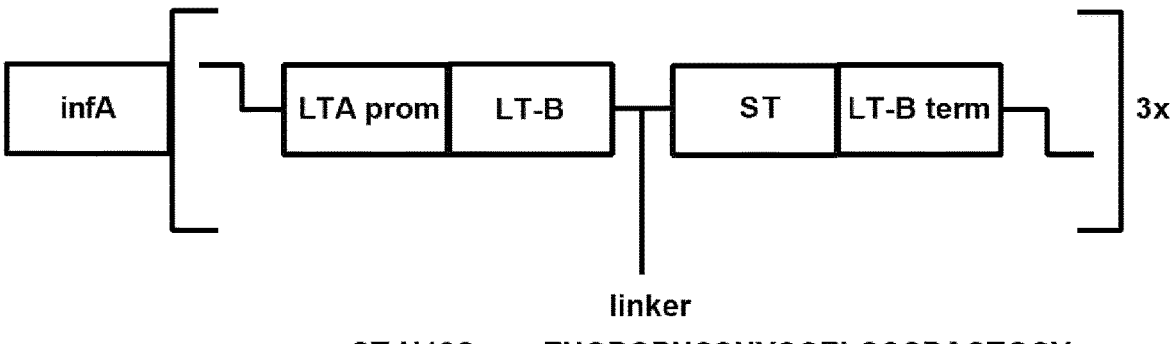

FIG. 1. Sequences referred to herein.

SEQ ID NO:19: Schematic illustration of the genetic construct as used in the Examples, which is carried by the large invasion plasmid of ShigETEC. LTB (coding sequence indicated in bold) is fused to ST(N12S) (coding sequence underlined) via a GPGP (SEQ ID NO:20) linker (encoded by a nucleotide sequence that is placed between the LTB and ST(N12S) coding sequences). ST is detoxified by an N12S mutation. Expression is driven by the LTA promoter (double underlined) and halted by the LTB termination sequence. The fusion gene is expressed as a 3× tandem repeat. The construct also expresses infA (in italic) as a separate gene with intrinsic promotor and terminator sequences. Sequence shown in FIG. 1: ENGPGPNSSNYC-CELCCSPACTGCY (SEQ ID NO:21)

Figure 2:
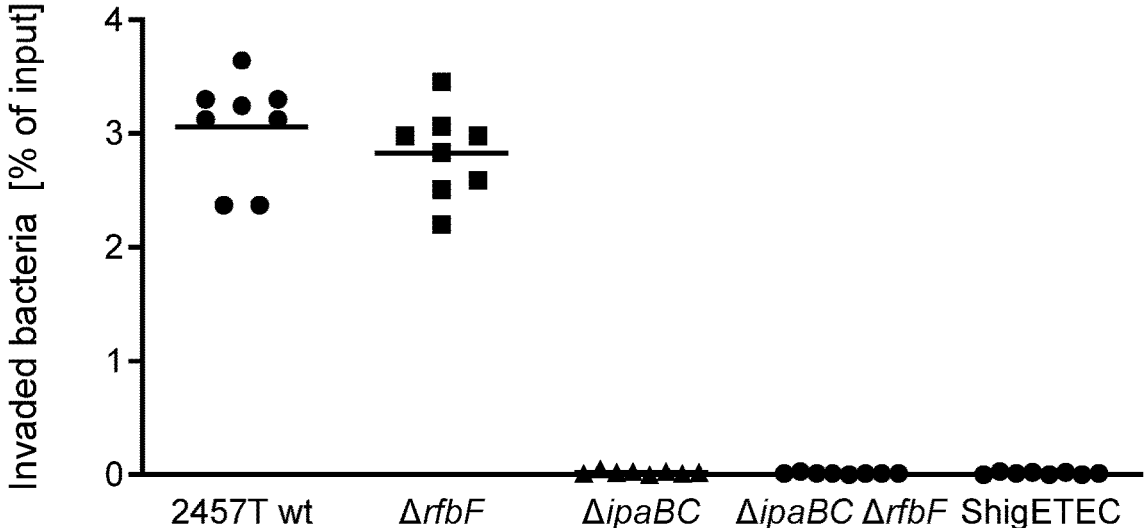

FIG. 2. HeLa cells were infected with the wild type parental *Shigella flexneri* 2a 2457T, ShigETEC, or corresponding isogenic mutants at a MOI of 80. Percentage of intracellular (invaded) bacteria relative to the inoculum was determined by CFU calculations after plating. Combined data of 4 biological replicates with 2 technical duplicates each are shown.

FIG. 3. Expression of detoxified ETEC antigens by ShigETEC. (a) ShigETEC whole cell lysates were tested for the expression of LTB-ST(N12S) by binding to the LTB receptor, GM1 in ELISA (grey bars). Bound LTB was detected by anti-CTB antibody. Expression level of LTB-ST(N12S) was compared to serially diluted LTB (black bars). A rough, non-invasive *Shigella* mutant (ΔrfbFΔipaBC) lacking the LTB-ST(N12S) fusion construct was used as negative control (white bar). (b) Wild type ST and its N12S mutant were generated recombinantly in *E. coli*. Supernatants (SN) of the cultures were used to stimulate T84 human epithelial cells and ST-induced cGMP production was measured by ELISA. Indicated amounts of synthetic ST were used as positive control. SN from bacteria carrying empty vector served as negative control. Triplicate measurements from two independent experiments were combined.

FIG. 4. ShigETEC induces protection against lethal challenge with heterologous *Shigella* strains. Mice were vaccinated 3 times i.n. with $10^8$ CFU ShigETEC (grey line) or buffer (black line). Four weeks after the last vaccination, mice were challenged i.n. with lethal doses of (a) *Shigella sonnei* ($9 \times 10^6$ CFU) or (b) *Shigella flexneri* 6 ($1.2 \times 10^7$ CFU). Survival was monitored for 14 days. Data from two independent experiments with a total of 10 mice per group are shown.

Figure 5:
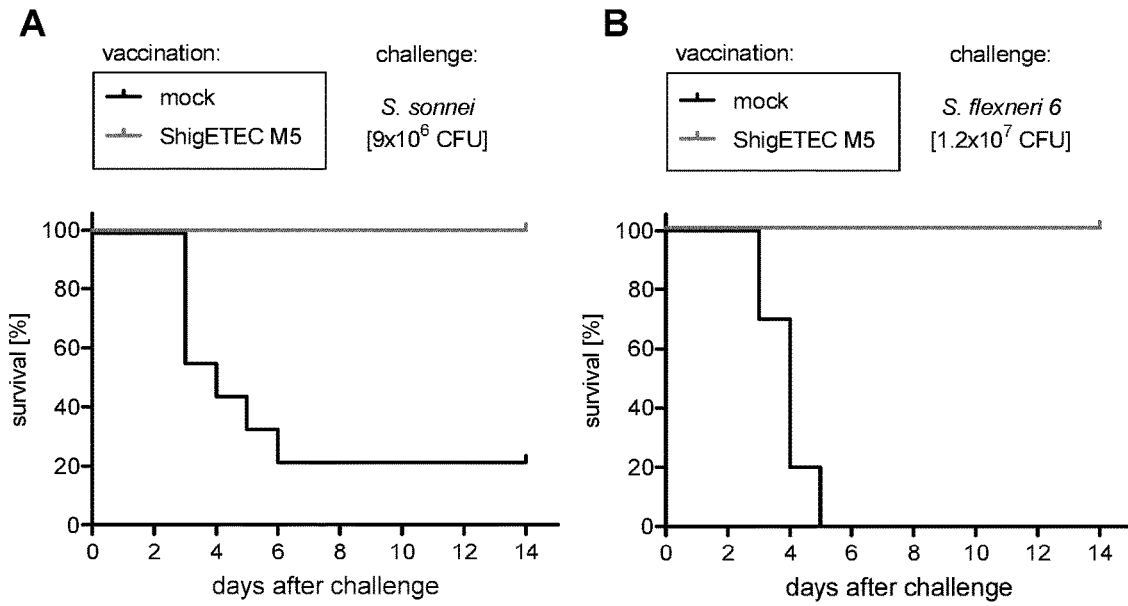

FIG. 5. Detection of serum IgG and mucosal IgA antibodies induced upon ShigETEC vaccination. (a) Mice were vaccinated 3 times i.n. with $10^8$ CFU ShigETEC. Specific IgG antibody levels were evaluated against indicated antigens in serum obtained 4 weeks after the last vaccination using the indicated serum dilutions in ELISA. Symbols represent averages of duplicate measurements of sera from individual mice (43 mice per group) from three independent vaccination experiments. (b) Mice were vaccinated 3 times i.n. with $10^8$ CFU ShigETEC and challenged with lethal doses of either *S. sonnei* or *S. flexneri* 6 four weeks after the last vaccination. Bronchoalveolar lavages (BAL) were taken two weeks after the challenge. Specific IgA antibody levels were evaluated against the indicated antigens using the indicated serum dilutions in ELISA. Symbols represent averages of duplicate measurement of BAL samples from individual mice from three independent vaccination experiments with 18 and 41 mice per group for mock and ShigETEC, respectively.

FIG. 6. Toxin neutralizing capacity of mouse sera induced by ShigETEC vaccination. (a) Mice were vaccinated 3 times i.n. with $10^8$ CFU ShigETEC. Serum at indicated dilutions was incubated with indicated amounts of LT, and LT-binding to GM1 coated plates was measured. Bound LT was detected with a polyclonal anti-cholera toxin antibody. (b) Sera from individual mice (3 times i.n. vaccinated with $10^8$ CFU ShigETEC (grey symbols) or buffer (mock, black symbols) were pre-incubated with the 5 ng LT. LT induced cAMP release was measured in T84 human colon epithelial cells.

FIG. 7. SEQ ID NO:19: the nucleotide sequence referred to in the Examples text (infA-3x[LTB-ST(N12S)]).

In the sequence: infA italic, LTB bold, ST(N12S): underlined (N12S mutation in bold and underlined), and the LTApromotor (double underlined); linker sequence between LTB and ST(N12S) (no emphasis added)

The LTB (coding sequence indicated in bold) is fused to ST(N12S) (coding sequence underlined) via a GPGP (SEQ ID NO:20) linker (encoded by a nucleotide sequence that is placed between the LTB and ST(N12S) coding sequences). ST is detoxified by an N12S mutation. Expression is driven by the LTA promoter (double underlined) and halted by the LTB termination sequence. The fusion gene is expressed as a 3× tandem repeat. The construct also expresses infA (in italic) as a separate gene with intrinsic promotor and terminator sequences.

FIG. 8 (example 8). Geometric mean titers of cohorts vaccinated with various CFUs of ShigETEC once (panel A) or with various number of times with a ShigETEC dose of 5×10^10 CFU (panel B). Serum samples collected at days 6, 10, 28, 60 after the (last) immunization were analysed for IgA titers reacting to the lysate of the vaccine strain in ELISA.

DETAILED DESCRIPTION OF THE INVENTION

Specific terms as used throughout the specification have the following meaning.

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−10% or +/−5% of the given value.

The term "antigen" as used herein shall in particular refer to any antigenic determinant, which can be possibly recognised by a binding site of an antibody. Specifically, preferred antigens are those molecules or structures, which have already been proven to be or are capable of being immunologically or therapeutically relevant, especially those, for which a clinical efficacy has been tested. The term as used herein shall in particular comprise molecules or structures selected from antigens comprising immunoaccessible and immunorelevant epitopes, in particular conserved antigens found in one or more species or serotype. Immunoaccessible epitopes are typically presented by or comprised in antigens expressed on the outer surface of a pathogen or on the surface of an infected cell.

The antigens may specifically include one or more immunologically relevant epitopes, which are herein understood as structures that are recognized by the subject's immune system and/or respective antibodies. Epitopes can e.g. be B-cell epitopes or T-cell epitopes, such as CD4+ T-cell epitopes or CD8+ T-cell epitopes. Antigens as described herein are specifically designed to trigger an immune response in a subject, and particularly include one or more antigenic determinants, which can be possibly recognized by a binding site of an antibody or are able to bind to the peptide groove of HLA class I or class II molecules or other antigen presenting molecules such as CD1 and as such may serve as stimulant for specific T-cells.

The term "attenuated" is used herein to describe a virulent strain of *Shigella* that has been modified so that it is no longer capable of causing disease, i.e., the modified strain is avirulent. The term "live" regarding the attenuated *Shigella* is used herein to describe *Shigella* that is able to grow and reproduce. Accordingly, the live *Shigella* strain described herein is used in the attenuated live vaccine and is specifically able to colonise the colon of a subject, but not cause the clinical symptoms associated with enteral diseases caused by the enteral or diarrheal pathogens. Further, the live strain described herein is specifically capable of limited replication in the vaccinated subject and of inducing a protective immune response which is protective against virulent strains of *Shigella*. An attenuated strain refers to an attenuated bacterium. Attenuation may comprise genetic engineering to produce mutants that differ from a native strain.

The attenuated *Shigella flexneri* strain described herein specifically is derived from a virulent strain of any of the respective *Shigella* serogroups (any serotypes of *Shigella flexneri*). For example, Serogroup B: *S. flexneri* (15 serotypes and subserotypes).

The virulent *Shigella* strain as used herein for the purpose of attenuation may be a clinically known virulent strain or a strain that is identified as containing virulence factors. Specifically, the strain is selected from any *S. flexneri*, in particular *S. flexneri* 2a, such as *S. flexneri* 2a 2457T (ATCC 700930, DNA=700930D-5), or CIP 107659 (Institute Pasteur, France), or any *S. flexneri* 2b strains.

The virulent *Shigella* strain may be modified by methods known in the art including multiple serial passage, temperature sensitive attenuation, mutagenesis, in particular targeted mutagenesis, or the like such that the resultant mutant strain is attenuated, specifically avirulent, not capable of causing disease in a subject.

In some embodiments, the modification to the virulent strain results in the deletion and/or inactivation of a gene, including reduction or suppression of expression of polynucleotides or genes encoding virulence factors or leads to the expression of non-functional virulence factors.

There are a number of techniques well known in the art to obtain attenuating mutations, e.g. for reducing or abolishing polynucleotide expression. For example, a mutation may be introduced at a predetermined site, such as the promoter region or within the coding sequence to produce a nonsense mutation, using recombinant DNA-technology. Recombinant DNA techniques comprise cloning the gene of interest, modification of the gene sequence by site-directed mutagenesis, restriction enzyme digestion followed by re-ligation and subsequent replacement of the wild type gene with the mutant gene.

Suitable standard recombinant DNA techniques are known in the art and described inter alia in Sambrook et al., "Molecular Cloning: A Laboratory Manual" (1989), 2nd Edition (Cold Spring Harbor Laboratory press).

Attenuating mutations may be performed employing methods well-known in the art, including cloning the DNA sequence of the wild-type gene into a vector, e.g. a plasmid, optionally inserting a selectable marker into the cloned DNA sequence or deleting a part of the DNA sequence, resulting in its inactivation. A deletion may be introduced by, for example, cutting the DNA sequence using restriction enzymes that cut at two points in or just outside the coding sequence and ligating together the two ends in the remaining sequence. Alternatively, a mutant allele in which the flanking regions of a target gene are amplified separately and linked directly together in a separate overlap PCR reaction, with omission of the intervening target sequence, can be constructed. A plasmid carrying the mutated DNA sequence can be transformed into the bacterium by known techniques such as electroporation chemical transformation or conjugation. It is then possible by suitable selection to identify a mutant wherein the inactivated DNA sequence has recombined into the chromosome of the bacterium and the wild-type DNA sequence has been rendered non-functional by homologous recombination.

Furthermore, if an antibiotic resistance gene is used, it is generally removed from the bacteria before they are used in a vaccine. According to the method of Datsenko et al. (Proc. Natl. Acad. Sci. U.S.A 97, 6640-6645 (2000)) mutagenesis is based on the lambda bacteriophage Red recombinase system that allows specific disruption of both plasmid encoded and chromosomal genes. The strategy is to replace such genes, e.g. with a selectable antibiotic resistance gene, which is generated by PCR using primers with 40-60 nt homology extensions to the targeted gene. The Red-based recombination is mediated in these homologous sequences. Following selection, the antibiotic resistance gene can also be eliminated using a helper vector that expresses the FLP recombinase, which uses FRT direct repeats (FLP recognition target) flanking the antibiotic resistance gene.

In certain embodiments, a mutation may be introduced at a predetermined site in chromosomal or extrachromosomal DNA, e.g. a plasmid, via an insertion, a deletion, or a substitution of one nucleotide by another, such as a point mutation, which leads to a mutated gene that has reduced or no expression. The mutation should produce a *Shigella* strain that has a reduced capacity to cause dysentery. Preferably, the mutation is a deletion mutation, where disruption of the gene is caused by the excision of nucleic acids. Such a mutation can, for example, be made by the deletion of a contiguous span of base pairs. Even very small deletions such as stretches of 10 base pairs can cause the gene to encode no protein or a non-functional protein. Even the deletion of one single base pair may lead to no protein or a non-functional protein, since as a result of such a mutation, the other base pairs are no longer in the correct reading frame or transcription has been inhibited or diminished. More preferably, a longer stretch is removed e.g. 100 base pairs or at least the significant part of a gene, e.g. at least 50% of the gene. Even more preferably, the whole gene is deleted.

Well-defined and deliberately made mutations involving the deletion of fragments or the whole gene, or combinations thereof, have the advantage, in comparison to classically induced mutations, that they will not revert to wild-type. Thus, in some embodiments described herein the vaccine strain comprises a live attenuated *Shigella* strain in which a mutation in a gene encoding a virulence factor comprises a deletion or an insertion to disrupt the polynucleotide sequence encoding the virulence factor so that no corresponding protein is produced or the protein is non-functional.

The attenuation may be, for example, by deleting and/or inactivating one or more of the following genes, or (a significant) part thereof, or any of the modulators of said gene effecting function of said genes: rfb, wzy, waaL aroA, aroC, aroD, aroE, guaA, guaB, virG and any one or more of ipaA-D. Preferred attenuated *Shigella* strains described herein are double mutants or multiple mutant strains with at least three or more attenuating mutations. Preferred combinations of target genes for attenuating mutations include at least one rfb gene (e.g. rfb F, D, C, E, J and/or I genes) and at least one ipa gene (e.g. ipaB, ipaC).

Techniques for identifying bacteria that have one or more mutations in genes encoding virulence factors are known by one skilled in the art. Accordingly, routine techniques for the detection of *Shigella* strains that have been mutated by the techniques described above include Northern and Western blotting, PCR, ELISAs and cytotoxicity assays as described elsewhere herein. Mutant strains with no functional genes encoding specific virulence factors can easily be selected employing standard techniques.

Genes encoding the virulence factors to be attenuated may be plasmid-borne. Therefore, in some embodiments the modification to a virulent *Shigella* strain comprises mutating one or more endogenous *Shigella* plasmids. The term "plasmid", specifically refers to cytoplasmic DNA that replicates independently of the bacterial chromosome. The mutation of parts of the *Shigella* virulence or invasion plasmid or even the elimination of a plasmid may be envisaged. However, it is preferred that the attenuated *Shigella* still comprises the endogenous invasion plasmid, more preferable a stable invasion plasmid. This ensures the stability of the attenuated strain, in particular with respect to the potential loss of the invasion plasmid by the attenuated cell, or the potential uptake of a (native) invasion plasmid derived from a wild-type *Shigella*, which may occur with an instable strain or instable invasion plasmid.

The *Shigella* invasion plasmid is endogenous in most strains of *Shigella*. Though the invasion plasmid may be lost on cultivating a *Shigella* strain, it may be engineered to obtain a recombinant one exhibiting a high level of stability, which renders it an attractive target for development as a useful vector to incorporate heterologous genes encoding antigens, in particular protective antigens.

A "cross-reactive" vaccine or respective immune response is understood as one which protects against infection by at least one different pathogen, e.g. a different serotype or bacterial species, which is not identical to the one used to elicit the response. Cross-protective efficacy typically may be tested with immune sera from subjects that had been exposed to the different pathogens reacted with different pathogens in ELISA or other immune assays.

The term "cross-reactive" as used herein with respect to antigens and an immune response to such antigens, shall refer to cross-serotype or cross-species reactions, providing immunity to one or more target serotypes and species, respectively. Cross-reactive vaccines as described herein can specifically trigger a cross-species immune response and respective immunoglobulins, e.g. by using a rough *Shigella* strain that is devoid of immunodominant O-antigens or ipa genes, to induce an immunoreaction that recognizes a series of target *Shigella* serotypes. An epitope or antigen can originate from one source species and be cross-reactive to a target species different from the source species. Epitopes can be shared between a series of species and therefore be cross-reactive. Cross-reactive epitope and antigens may trigger a cross-species reactive immune response and respective cross-reactive immunoglobulins.

The (cross-)reactivity against a certain target pathogen can e.g. be determined by immunological methods, e.g. ELISA, FIA, RIA, fluorescent microscopy, or flow cytometry.

When a cross-reactive antigen is designed to induce cross-protective immunity, this may be tested in animal models, e.g. by immunising the animals with the cross-reactive antigen derived from one pathogen triggering an immune response, and challenging the animals with at least one pathogen different form the one used to elicit the response. As an example, such cross-protective immunity against more than one *Shigella* serotype or other enteroinvasive bacteria with cross-reactive antigens, such as *E. coli*, specifically refers to protection against distinct variations within the species of bacteria of different individuals, e.g. variations at the sub-species level. The group of serovars with common antigens is called a serogroup or serotype.

The basis for the development of a broad spectrum, e.g. multi-strain and/or multi-serotype and/or multi-species *Shigella* vaccine is the identification of cross-reactive antigens which are prevalent in *Shigella* serovars. This particularly includes isolates associated with human infections.

When a polyvalent vaccine is designed to induce cross-protective immunity against different pathogens, the immune response typically is elicited by several antigens, e.g. individual antigens from the different pathogens. As an example, such polyvalent vaccine may be based on at least two different protective antigens from different species, such as derived from *Shigella* and *Escherichia*, but also other bacterial, viral, fungal or parasitic antigens. The cross-protective, polyvalent vaccine may e.g. be tested in an animal model by immunizing the animals with the vaccine comprising different protective antigens derived from at least two different pathogens triggering an immune response, and challenging the animals with one, two or more of the pathogens.

The basis for the development of a multi-species vaccine candidate based on specific attenuated *Shigella* bacteria, as described herein, is the identification of protective antigens, either cross-reactive to address a series of different serotypes or not, which are prevalent in the different pathogenic species, against which protection is sought.

The term "enteral" also known as "enteric", as used herein specifically in connection with a disease or pathogen shall refer to a disease condition or pathogen relating to, or affecting the intestines, e.g. dysentery or diarrheal disease. Specifically, such enteral disease refers to infectious disease of the colon. Specific symptoms include bloody, mucus-filled diarrhea; abdominal pain; fever and loss of fluids from the body. Diarrheal disease refers to conditions resulting in three or more loose or liquid stools per day, or as having more stools than is normal for that person. An enteral pathogen is understood to cause enteral disease in a subject, either upon infection with said pathogen, or intoxication of the subject with a toxin, in particular an enterotoxin.

There are many causes of infectious enteral disease, such as dysentery or diarrhea, which include viruses, bacteria, fungi and parasites. Examples are provided as follows: Norovirus is the most common cause of viral diarrhea in adults, but rotavirus is the most common cause in children under five years old. Adenovirus types 40 and 41, and astroviruses cause a significant number of infections. The bacterium *Campylobacter* is a common cause of bacterial dysentery or diarrhea, but infections by Salmonellae, Shigellae and some strains of *Escherichia coli* (*E. coli*) are frequent in some territories. In the elderly, particularly those who have been treated with antibiotics for unrelated infections, a toxin produced by *Clostridium difficile* often causes severe diarrhea. Examples of parasites include *Giardia lamblia*, which can cause chronic infections, and *Entamoeba histolytica*. Examplary enteral disease as possibly addressed by the vaccine described herein is Shigellosis and ETEC-related diarrhea.

The term "endogenous" as used herein with respect to a plasmid shall mean the plasmid that is naturally-occurring in a particular (wild-type) host cell. An endogenous plasmid may be genetically engineered to obtain a recombinant endogenous plasmid, e.g. by recombinant techniques to engineer the plasmid in situ, i.e. within the host cell harbouring the native endogenous plasmid, or else upon removal from the host cell, subjecting it to laboratory manipulation, and then reintroduced into a host cell of the same type. The invasive phenotype of *Shigella* is specifically conferred by the endogenous 220-kb virulence plasmid, also called invasion plasmid, or native or endogenous invasion plasmid. The endogenous invasion plasmid of *Shigella* is specifically provided as described herein for recombination purposes, either as isolated invasion plasmid or for in situ recombination.

The term "endogenous" is also used to specify a nucleotide sequence or a gene of the *Shigella* strain as described herein. Such nucleotide sequence or gene is understood to be an element endogenous to *Shigella*, if naturally-occurring, such as present in a native, wild-type *Shigella* strain, in particular wherein such element is positioned within the genome where naturally-occurring without replacement.

The *Shigella* endogenous invasion plasmid is well characterized in the art, and this knowledge informs selection of sites for recombination in such plasmids, as well as appropriate propagation conditions, e.g. at position between ntds 103187-103328 between an IS100 and ipaJ genes (these positions are determined for the pCP301 invasion plasmid of the *Shigella flexneri* 2a 301 strain)

The term "essential" as used herein with respect to a gene is understood to refer to a gene necessary for a living organism to survive, e.g. for a bacterial cell to replicate. Mutation of an essential gene, such as a deletion and/or inactivation, would cause a lethal phenotype or a non-replicable cell. Essential genes of *Shigella* may be mutated to delete the gene(s) of the *Shigella* chromosome, and further to incorporate the gene(s) into the invasion plasmid to stabilize the invasion plasmid. This provides for cultivation of a *Shigella* with a stable recombinant endogenous invasion plasmid. Among the essential genes of *Shigella* there are the ppa, accD, acpS, dapE, era, frr, ftsI, ftsL, ftsN, ftsZ, infA, lgt, lpxC, msbA, murA, murI, nadE, parC, proS, pyrB, rpsB, trmA, rho and rhoL genes.

The term "heterologous" is herein used to refer to an element, such as e.g., an expression construct, gene, antigen, or epitope, being part of a larger structure, such as a nucleic acid molecule, plasmid, polypeptide or protein, which is foreign to the other parts of such larger structure.

With regard to a heterologous expression construct described herein, the term specifically refers to an expression cassette that is not naturally incorporated into the genome or into the endogenous invasion plasmid of the *Shigella* strain that has not been genetically engineered to incorporate said expression cassette.

An expression construct is also understood as being heterologous, if comprising an artificial expression construct, such as e.g. comprising a promoter operably linked to a gene wherein the promoter is not naturally controlling expression of said gene in a wild-type *Shigella* strain.

A nucleotide sequence, gene, or expression construct is herein understood as being an element that is heterologous, if transpositioned or positioned at a different genomic region as compared to a wild-type *Shigella* strain. For example, where such element is understood to be heterologous to the invasion plasmid, if originating from a chromosomal region of *Shigella* and incorporated into the invasion plasmid. For example, an expression construct incorporated into the invasion plasmid and expressing a chromosomal gene of *Shigella* is herein understood to be heterologous to the invasion plasmid.

Expression systems, genetic constructs or modifications described herein may employ tools, methods and techniques known in the art, such as described by J.

Sambrook et al., Molecular Cloning: A Laboratory Manual (3rd edition), Cold Spring Harbor Laboratory, Cold Spring Harbor Laboratory Press, New York (2001). Expression vectors may include but are not limited to cloning vectors, modified cloning vectors and specifically designed plasmids.

Specific expression constructs described herein are comprising a nucleic acid sequence to be expressed and regulatory elements in operable linkage (thereby operably controlling expression of said nucleic acid sequence) as necessary to express said gene in a host cell. Examples of regulatory sequences include promoter, operators, enhancers, ribosomal binding sites, and sequences that control transcription and translation initiation and termination. Specific expression constructs are expression cassettes comprising a promoter operably linked to a DNA sequence to be expressed, i.e. where expression of the DNA sequence is under control of said promoter.

With regard to a heterologous antigen described herein, the term specifically refers to antigens that are not naturally expressed in the *Shigella* strain that has not been genetically engineered to express said antigen. An antigen is also understood as being heterologous, if comprising a mutation in the antigen sequence which is not naturally-occurring in the wild-type *Shigella* strain.

The *Shigella* strain described herein may be genetically engineered to express a heterologous antigen, e.g. a nontoxic component or form of LT and/or ST, such as a mutant ST (STm). Specifically, STm differs from the wild-type ST in at least one or two point mutation(s), such as an amino acid substitution. Such cells induce an immune response against the heterologous antigen as well as the native antigens and hence improve the protection provided by a vaccine.

Herein "inactivation" of a gene is always understood to refer to transient, inducible or constitutive down-modulation of a gene, so to reduce or inhibit expression of a gene product. This may specifically be done by mutation of a gene or regulatory sequence operably linked to the gene, such as promoters, enhancers, etc. that regulate the expression of a gene. Among the inactivating mutations there are particularly those that result in the reduction or suppression of expression of polynucleotides or genes, e.g. genes encoding virulence factors, or lead to the expression of respective non-functional proteins, e.g. non-functional virulence factors.

The term "invasive" or "non-invasive" as used herein with respect to a gene is understood in the following way. Invasive pathogenic bacteria are capable of invading eukaryotic cells. For example, after invasion, *Shigella* may multiply intracellularly and spread to neighbouring epithelial cells, resulting in tissue destruction and characteristic pathology of Shigellosis. Among the genes mediating invasiveness of *Shigella* there are e.g., the ipa genes encoding invasion plasmid antigens. Deletion and/or inactivation of at least one of such genes may lead to a non-invasive *Shigella*.

The epithelial cell invasion test is a standard in vitro test for determining invasiveness of a *Shigella* strain. Invasion and intracellular growth are determined using e.g., HeLa cells (human epithelial cells). A *Shigella* strain is determined to be non-invasive, if no invasion of the epithelial cells is observed (less than the detection minimum) as compared to a control (an invasive (e.g., wild-type) *Shigella* strain), after an incubation time (of e.g., at least 30, 40, 50, or 60 min), that allows the control to invade at least about 10% or 20%. In such test, a strain is considered non-invasive where the percentage of invaded cells are e.g., less than 2% or less than 1%.

The Sereny test is an additional standard in vivo (non-human animal) test for determining the invasiveness of organisms such as *Shigella* or enteroinvasive *Escherichia coli* (EIEC). (Wood et al. J. Clin. Microbiol. 24: 498-500, 1986). It is done by inoculating suspension of bacteria into guinea pig's eye. Severe mucopurulent conjunctivitis and severe keratitis indicates a positive test. A strain is determined to be non-invasive or avirulent, if no signs of keratoconjunctivitis is observed.

The term "rough" with respect to a gram-negative bacteria, such as *Shigella*, means other than smooth, and shall specifically include "gently-rough" (i.e. O-antigen synthesis downregulated) or "semi-rough" (one single O-antigen repeat expressed) or "deep-rough" (LPS core is truncated) bacteria. The term "rough" as used herein may include characteristics such as an irregular colony morphology, and may include for instance undulate and/or lobate morphology. The term specifically means that a strain is unable and/or substantially unable to produce O-polysaccharide. A repetitive glycan polymer contained within an LPS is referred to as the O-antigen, O-polysaccharide, or O-(side-) chain of Gram-negative bacteria. The O antigen is attached to the core oligosaccharide and comprises the outermost domain of the LPS molecule. The presence or absence of the O-chains determine, whether the LPS is considered rough or smooth. Bacterial strains that have altered O-antigen structures change their appearance from smooth to dull when grown on agar plates. Full-length O-chains make the LPS smooth, while the absence or reduction of O-chains renders the LPS rough. "Smooth" bacteria include the complete core and O-antigen. "Rough" bacteria include a lack of LPS O-antigen, meaning no O-antigen or a reduced chain length of O-antigen or a reduced number of smooth LPS chains. The term "Gently-rough" refers to a subgroup of rough bacteria, which have a reduced chain length of O-antigen or a reduced number of smooth LPS chains. "Deep rough" bacteria are a subgroup of rough bacteria, which have lost parts of the LPS core, consequently lack O-antigens as well. "Semi-rough" mutants are a subgroup of rough bacteria, which express one single O-antigen repeat on LPS-core due to the loss of function of the O-antigen polymerase enzyme.

The term "reduction of LPS O-antigens" as used herein with respect to rough *Shigella* shall specifically refer to less than 50%, or less than 40%, or less than 30%, or less than 20%, or less than 10%, or essentially no or no LPS O-antigen as determined in a standard assay.

A standard test may be used to determine the rough characteristics of a strain.

For example, the phenotype of LPS mutants may e.g., be determined by SDS-PAGE separation of LPS and silver staining or agglutination tests using O-antigen-specific immune sera.

The rough *Shigella* may be produced by mutation of at least one gene or a significant part thereof, such as by deletion and/or inactivation, which gene is involved in the LPS synthesis, transport and/or expression, preferably selected from the group consisting of genes in the cluster of the rfb operon, or one or more of genes within the rfb/wbb gene cluster encoding O-antigen synthesis, waaL encoding the O-antigen ligase, wzx encoding O-antigen flippase involved in O-antigen transport, wzy/rfc involved in O-antigen polymerization, genes within the rfa/waa gene cluster encoding LPS-core synthesis, regulatory genes affecting O-antigen expression, such as rfaH, or loss of function(s) of which results in at least 90% reduction in the expression of O-antigens.

Specific examples of genes involved in the LPS sugar synthesis are rfbA, B, D and C.

Specific examples of genes involved in the LPS sugar transferase are rfbF and G.

A specific example of a gene involved in the LPS O-antigen polymerase is rfc/wzy.

The cluster of the rfb operon is located either on the chromosome or on the invasion plasmid (*Shigella sonnei*). Specific genes in this cluster are rfb F, D, C, E, J and/or I genes.

The term "set" or "setBA" as used herein shall refer to the gene(s) endogenous to *Shigella* and encoding a *Shigella* enterotoxin (ShET), in particular ShET1, e.g. as described by Kotloff et al. (2000, 2004, or 2007).

The term "sen" as used herein shall refer to the gene endogenous to *Shigella* and encoding *Shigella* enterotoxin 2 (ShET2), e.g. as described by Kotloff et al. (2000, 2004, or 2007).

The term "origin" as used herein with respect to an antigen originating from a pathogen, is herein understood to define a respective amino acid sequence which is identical to the respective sequence as naturally-occurring in the pathogen, which may be used as a source of said antigen, and which can be used as a template to produce a modified sequence by modifying the naturally-occurring (source) sequence, thereby producing a mutant or derivative thereof. Such mutant is herein understood as a mutant originating from the source.

As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments.

The term "recombinant" as used herein specifically means "being prepared by or the result of genetic engineering" i.e., by human intervention. A recombinant nucleotide sequence may be engineered by introducing one or more point mutations in a parent nucleotide sequence, and may be expressed in a recombinant host cell that comprises an expression cassette including such recombinant nucleotide sequence. The polypeptide expressed by such expression cassette and host cell, respectively, is also referred to as being "recombinant". For the purpose described herein conventional molecular biology, microbiology, and recombinant DNA techniques within the skill of the art may be employed. Specific embodiments described herein refer to the production of a chimeric antigen, and the recombinant means for such production, including a nucleic acid encoding the amino acid sequence, an expression cassette, a vector or plasmid comprising the nucleic acid encoding the amino acid sequence to be expressed, and a host cell comprising any such means. Suitable standard recombinant DNA techniques are known in the art and described inter alia in Sambrook et al., "Molecular Cloning: A Laboratory Manual" (1989), 2nd Edition (Cold Spring Harbor Laboratory press).

Herein the term "subject" is understood to comprise human or warm-blooded mammalian subjects, such as human beings or livestock animals (particularly including e.g., pigs), companion animals, and laboratory animals, which subjects are either patients suffering from a specific disease condition or healthy subjects. The term "subject" includes those receiving either prophylactic or therapeutic treatment.

In particular, the treatment and medical use described herein applies to a subject in need of prophylaxis or therapy of a disease condition associated with a pathogen infection. Specifically, the treatment may be by interfering with the pathogenesis of a disease condition where a pathogen is a causal agent of the condition. The subject may be a subject at risk of such disease condition or suffering from disease.

The term "at risk of" a certain disease conditions, refers to a subject that potentially develops such a disease condition, e.g. by a certain predisposition, exposure to a pathogen or pathogen-infected subjects, or that already suffers from such a disease condition at various stages, particularly associated with other causative disease conditions or else conditions or complications following as a consequence of pathogen infection.

The term "treatment" as used herein shall always refer to treating subjects for prophylactic (i.e., to prevent infection and/or disease status) or therapeutic (i.e. to treat diseases regardless of their pathogenesis) purposes. The vaccine preparation described herein is specifically provided for active immunotherapy.

Specifically, the term "prophylaxis" refers to preventive measures which is intended to encompass prevention of the onset of pathogenesis or prophylactic measures to reduce the risk of pathogenesis.

The term "therapy" as used herein with respect to treating subjects refers to medical management of a subject with the intent to cure, ameliorate, stabilize, reduce the incidence or prevent a disease, pathological condition, or disorder, which individually or together are understood as "disease condition".

The vaccine described herein specifically comprises the *Shigella* cells in an effective amount, which is herein specifically understood as "effective amount" or "immunologically effective amount". By "immunologically effective amount", it is meant that the administration of that amount to a subject, either in a single dose or as part of a series of doses, is effective on the basis of the therapeutic or prophylactic treatment objectives. A "prophylactically effective amount" refers to an amount effective, at dosages and for periods of time necessary, to achieve the desired prophylactic result, such as preventing a target pathogen infection, or inhibiting a target pathogen disease onset or progression. This amount will vary depending upon the health and physical condition of the subject to be treated, age, the capacity of the subject's immune system to synthesize antibodies, the type and degree of immune response desired, the formulation of the vaccine, and other conditions.

An effective amount or dosage may be provided as a certain amount of colony-forming units (CFU), which determines the number of viable bacteria in a preparation.

The term "CFU" is an abbreviation of the term "colony-forming unit" and used herein to quantify the number of viable bacteria in a preparation. Counting with colony-forming units requires culturing the microbes and counts only viable cells, in contrast to microscopic examination which counts all cells, living or dead. The number of CFU is typically determined by the number of cells present in a sample which are able to give rise to colonies under specific conditions of nutrient medium, temperature and time. The CFU results may be obtained by microbiological plating and counting methods. Typically, serial dilutions from a bacterial suspension are plated onto appropriate agar plates (e.g., LB-agar, or TSA) and incubated for 16-24 hours at 37° C. Subsequently, the colonies formed at appropriate dilutions are enumerated and the obtained number multiplied by the dilution factor determines the bacterial concentration (i.e., CFU/ml) of the initial bacterial suspension.

The vaccine preparation described herein may be administered as a high dose treatment of a subject in the course of an active immunotherapy to prevent enteral disease, specifically dysentery caused by *Shigella* and optionally heterologous enteral or diarrheal pathogens. This may be achieved by a vaccine described herein, which is cross-protective and/or polyvalent.

For example, the effective dosage is capable of eliciting an immune response in a subject of effective levels of antibody titer to bind and neutralize the target pathogen, e.g., 1-3 months after immunization. The effectiveness can be assayed by the respective antibody titers in samples of blood taken from the subject.

In some embodiments, an effective amount is one that has been correlated with beneficial effect when administered as part of a particular dosing regimen, e.g. a single administration or a series of administrations such as in a "boosting" regimen. For treatment, the vaccine described herein may be administered at once, or may be divided into the individual components and/or a number of smaller doses to be administered at intervals of time. Typically, upon priming a subject by a first administration of a vaccine described herein, one or more booster administrations may be performed over a period of time by the same or different administration routes. Where multiple administrations are used, subsequent administrations may be made, e.g., within any one of 1, 2, 3, 4, 5, 6, days; or within any one of 1, 2, 3, 4, 5, 6, 7, or 8 weeks; or within any one of 2, 3, 4, 5, 6, 7, 8, 9, 10, 11 or 12 months (e.g., within 1 to 52 weeks) of the previous administration.

The vaccine described herein may comprise the *Shigella* cells in a pharmaceutical preparation which optionally comprises an immunogenic formulation. Specific embodiments comprise pharmaceutically acceptable excipients or carriers.

Pharmaceutical carriers suitable for facilitating certain means of administration are well known in the art. Specific embodiments refer to immunogenic formulations, which comprise a pharmaceutically acceptable carrier and/or adjuvant, which trigger a humoral (B-cell, antibody) or cytotoxic (T-cell) immune response. Adjuvants may specifically be used to enhance the effectiveness of the vaccine. Adjuvants may be added directly to the vaccine compositions or can be administered separately, either concurrently with or shortly before or after administration of the vaccine antigen.

The term "adjuvant" as used herein specifically refers to a compound that when administered in conjunction with an antigen, it augments and/or redirects the immune response to the antigen, but when administered alone does not generate an immune response to the antigen. Adjuvants can augment an immune response by several mechanisms including lymphocyte recruitment, stimulation of B- and/or T-cells, and stimulation of macrophages.

The vaccine described herein may be formulated using known techniques for formulating attenuated bacterial vaccines. The vaccine is advantageously presented for oral administration, for example as an aqueous solution or dried powder for reconstitution in a suitable buffer prior to administration. Reconstitution is advantageously effected in a buffer at a suitable pH to ensure the viability of the bacteria.

In order to protect the attenuated bacteria and the vaccine from gastric acidity, a protective agent, such as sodium bicarbonate is advantageously administered with each administration of the vaccine. Alternatively, the vaccine is presented in a lyophilized encapsulated form.

Vaccine strains may be administered in a pharmaceutically acceptable vehicle, e.g., as a spray or mixed in food and/or water or delivered in admixture with a suitable carrier, diluent, adjuvant or excipient such as sterile water, physiological saline, glucose, or the like. The vaccine strains may contain auxiliary substances such as wetting or emulsifying agents, pH buffering agents, adjuvants, gelling or viscosity enhancing additives, preservatives, flavoring agents, colours, and the like, depending upon the route of administration and the preparation desired. Pharmaceutical carriers for preparation of pharmaceutical compositions and medicaments are well known in the art, as set out in textbooks such as "Remington's Pharmaceutical Sciences" (1990), 18th Edition (Mack Publishing Co.).

Pharmaceutically acceptable carriers generally include any and all suitable solvents, dispersion media, coatings, preservatives such as antibacterial (in particular an agent that is not anti-*Shigella* effective) and antifungal agents, isotonic and absorption delaying agents, and the like that are physiologically compatible with a bacterial preparation as described herein. Specific examples of pharmaceutically acceptable carriers include sterile water, saline, phosphate buffered saline, dextrose, glycerol, ethanol, polyethylene glycol, and the like, as well as combinations of any thereof. Additional pharmaceutically acceptable carriers are known in the art and described in, e.g., Remington: The Science and Practice of Pharmacy, $22^{nd}$ revised edition (Allen Jr, LV, ed., Pharmaceutical Press, 2012). Liquid formulations can be solutions, emulsions or suspensions and can include excipients such as suspending agents, solubilizers, surfactants, preservatives, and chelating agents. Exemplary carriers are liposomes or cationic peptides. According to a specific example, herein referred to as ShigETEC, the formulation is a concentrate of live bacteria in a PBS buffer containing 10% PEG-6000 for oral delivery, which can be stored and provided in the frozen form.

The preferred preparation is in a ready-to-use, storage stable form, with a shelf-life of at least one or two years. The invention also provides a delivery device, e.g. a syringe, pre-filled with the vaccine described herein.

The vaccine described herein can be administered by conventional routes known the vaccine field, in such as to a mucosal (e.g., ocular, intranasal, oral, gastric, intestinal, rectal) surface, or topical administration (e.g., via a patch).

The vaccine strains described herein can be administered in dosages and by techniques well known to those skilled in the medical or veterinary arts, taking into consideration such factors as the age, sex, weight, species and condition of the recipient subject, and the route of administration. Vaccine strains can be administered alone, or can be co-administered or sequentially administered with other treatments or therapies. Forms of administration may include suspensions, syrups or elixirs, such as sterile suspensions or emulsions.

The foregoing description will be more fully understood with reference to the following examples. Such examples are, however, merely representative of methods of practicing one or more embodiments of the present invention and should not be read as limiting the scope of invention.

EXAMPLES

Example 1. Generation of the ShigETEC Vaccine Strain

The fully sequenced *Shigella flexneri* strain 2457T (Genbank accession #: ADUV00000000.1) harboring the ~200

Kbp (140 MDa) large invasion plasmid was used as the parental strain (Wei et al. Infect Immun 2003, 71, 2775-2786). For genetic manipulations the Red recombinase method was used (Datsenko and Wanner, Proc. Natl. Acad. Sci. U.S.A 97, 6640-6645 (2000)). To remove the serotype-determining and dominant antigen that would allow sero-type-independent protection, the wild-type parental strain was rendered rough—that is lacking expression of the LPS O-antigen—by deletion of the rfbF gene from the chromosome. With the aim to generate a non-invasive vaccine strain for oral use, two genes involved in the function of the type III secretion system, ipaB and ipaC, were deleted from the invasion plasmid (IP). Moreover, to reduce the risk of reactogenicity of the vaccine, the *S. flexneri* 2 specific putative enterotoxin ShET-1, an AB5 toxin similar to cholera toxin and LT (Kotloff et al. 2004), was also removed by deletion of the genes setBA from the chromosome, a step that also eliminated the virulence factor Pic that is encoded at the same locus on the complimentary DNA strand.

To provide additional ETEC coverage for the vaccine, a synthetic fusion gene was constructed, which encodes a chimeric LTB-STm fusion toxoid.

The amino acid sequence of the LTB-STm fusion toxoid is identified by SEQ ID NO:12. The coding nucleotide sequence is identified by SEQ ID NO:13.

The LTB subunit is not toxic in the absence of the LTA subunit of the LT holotoxin, while the ST peptide is inherently toxic. Therefore, the N12S mutation was introduced into the ST gene. This mutation had been shown to eliminate toxicity while retaining antigenicity of ST (Taxt et al. Infect Immun 2016, 84, 1239-1249). To ensure higher expression levels a triple tandem of the LTB-mST fusion protein gene was inserted into the IP. The insert was supplemented with the infA gene, a single copy essential gene (Cummings et al. J Bacteriol 1994, 176, 198-205), which was subsequently removed from the chromosome to achieve invasion plasmid stabilization (Schuch et al. Infect Immun 1997, 65, 3686-3692). The schematic structure of this synthetic construct as well as the sequence of the ST toxoid and the linker region between LTB and the ST toxoid is illustrated in FIG. 1.

The resulting strain is designated *Shigella flexneri* 2457TΔrfbFΔipaBCΔinfAΔsetBA::infA-3x[LTB-ST (N12S)], or ShigETEC. To demonstrate that all intended genetic manipulations were successfully accomplished in the ShigETEC strain, all expected phenotypic changes were verified by PCR and sequencing.

CFU Determination

ShigETEC is routinely grown in tryptic soy broth (TSB), washed in PBS and concentrated to the desired CFU/ml in formulation buffer. Frozen stocks are kept at −80 C.

The enumeration of the exact CFU in the vaccine preparation is determined by plating. Appropriate dilutions are made in PBS. The choice which dilutions are prepared and plated depends on the expected CFU of the starting material. In order to obtain a countable number of bacterial colonies, which is more or equal to 10 and less or equal to 250, 100 μl of at least 3 dilutions is spread on TSA plates in duplicates. For example, for the expected number of CFUs, the following dilutions could be plated:

| Expected CFU | dilutions for plating | | |
|---|---|---|---|
| $1 \times 10^9$ | $5 \times 10^4$ | $1 \times 10^5$ | $2 \times 10^5$ |
| $1 \times 10^{10}$ | $5 \times 10^5$ | $1 \times 10^6$ | $2 \times 10^6$ |

-continued

| Expected CFU | dilutions for plating | | |
|---|---|---|---|
| $5 \times 10^{10}$ | $2 \times 10^6$ | $5 \times 10^6$ | $1 \times 10^7$ |
| $2 \times 10^{11}$ | $5 \times 10^6$ | $1 \times 10^7$ | $2 \times 10^7$ |

Serial dilutions in sterile PBS are prepared in 15 ml tubes. The smallest volume of sample for a 1/10 dilution is 500 μL added to 4.5 mL dilution medium. For a 1/10 dilution 1 volume of sample to 9 volumes of diluent is added.

100 μl of the appropriate dilution of the sample are plated in duplicates or triplicates (2 or 3 plates per dilution) and incubated at 37° C. during 16 to 24 hours. CFUs (colonies that appear on the agar plates) are counted on the next day. The real CFU/ml of the original vaccine preparation is determined by multiplying the average of the counted CFUs by the dilution factors.

Example 2. Phenotypic Characterization of ShigETEC

2.1. ShigETEC Expresses Rough Lipopolysaccharide

As a result of rfbF deletion, complete loss of O-antigen was demonstrated by the lack of O-antigen ladder on a silver-stained gel characteristic of LPS preparations from wild type *Shigella* strains. The lack of agglutination of the vaccine strains with an anti-*Shigella flexneri* typing serum confirmed the lack of O-antigen expression.

2.2. ShigETEC is Non-Invasive and Avirulent

Invasion of human epithelial cells is an inherent characteristic of *Shigella* and requires the function of the Type III secretion apparatus. Deletion of the ipaB and ipaC is expected to result in loss of invasive capacity of ShigETEC. This was confirmed in an in vitro invasion assay using HeLa (human epithelial) cells. While the parental wild type strain was able to invade the cells, ShigETEC completely lost its invasive capacity (FIG. 2). The single rough mutant lacking rfbF only, showed invasiveness similar to the wild-type strain. On the other hand, the single mutant AipaBC was found completely non-invasive such as ShigETEC. These data clearly demonstrate that from the multiple mutations in ShigETEC, deletion of rfbF does not contribute to the non-invasive phenotype in this assay.

The Sereny test is the gold standard in vivo model to assess the virulence of *Shigella* strains widely used to confirm attenuation before clinical testing in human volunteers (Sereny, B. Acta Microbiol Acad Sci Hung 1955, 2, 293-296). It is performed by inoculation of bacterial suspension in the eye of guinea pigs with virulent *Shigella* strains causing severe keratoconjunctivitis. To test the virulence of ShigETEC in this model ocular inoculation of guinea pigs was performed with ShigETEC or its wild-type parent strain (*S. flexneri* 2a 2457T). The parental wild type strain induced keratoconjunctivitis with severity scores proportional to the inoculum size while the vaccine strain was completely avirulent even at the highest bacterial inoculum In summary, in vitro and in vivo assays have proven the non-invasiveness and avirulence of ShigETEC. This is fully in line with expectations due to the essential roles of IpaB and IpaC in the function of the T3SS and invasiveness.

Methods: Invasiveness of the ShigETEC vaccine strain as well as isogenic single mutants (ΔrfbF or ΔipaBC) was assessed in vitro using epithelial cells. Invasiveness was compared to that of the parental wild-type strain 2457T. HeLa cells (ATCC, CCL-2) were grown in Dulbecco's Modified Eagle Medium (DMEM) with 10% FCS in 24-well plates until confluency. Cells were infected with wild type or vaccine strain at a multiplicity of infection (MOI) of 80 for 1 h at 37° C. After incubation, plates were washed twice with Phosphate-buffered saline (PBS) and the extracellular bacteria killed with 50 μg/ml gentamycin (30 min at 37° C./5% $CO_2$). Cells were washed 3 times with PBS before lysis with 1% Triton X-100. Bacteria were quantified by plating onto tryptic soy agar (TSA) plates. Percentages of invasive (intracellular) bacteria was calculated relative to the bacterial numbers in the inoculum determined by plating onto TSA.

In the Sereny test, female, guinea pigs (4-5 months of age, Charles River) were inoculated in the left eye with ShigETEC and in the right eye with its wild-type parental strain (*S. flexneri* 2457T) at bacterial doses of $10^6$-$10^9$ colony forming units (CFU)/eye (suspended in 50 μl of PBS). Two identical independent experiments were performed with 4 animals each (2 animals per dose in total). Animals were monitored for 6 days post-infection and the severity of symptoms (mucopurulent conjunctivitis and keratitis) were scored on a scale of 0-4.

Example 3: ShigETEC Expresses Detoxified ETEC Toxin Antigens

Expression of the fusion protein of LTB and ST(N12S) was demonstrated and quantified by ELISA based on GM1 (i.e LTB receptor) binding using lysates of ShigETEC cultures collected in different growth phases. The fusion toxoid was expressed at all growth phases with higher expression upon increasing bacterial concentration (FIG. 3*a*). Specificity of the detection was shown using lysates from a ΔrfbFΔipaBC mutant that did not carry the chimeric toxin antigen element (FIG. 3*a*).

Complete detoxification of the ST(N12S) mutant was demonstrated by the lack of cGMP induction in T84 human epithelial cells after exposure to supernatants of *E. coli* cultures expressing recombinant wild type ST or ST(N12S) (FIG. 3*b*).

Methods: Detection of LTB-ST(N12S) fusion protein expression: ShigETEC whole cell lysates were prepared from cultures grown to $OD_{600\ nm}$ 0.5, 2 or overnight (O/N). Expression of the LTB-ST(N12S) fusion protein was determined by GM1 binding. ELISA plates were coated with 10 μg GM1 (Sigma-Aldrich) per well at 4° C. OX/N. Plates were blocked with 2% bovine serum albumin (BSA, Fisher Scientific) for 1 h at room temperature (RT). Recombinant LTB (Sigma-Aldrich) was used in serial dilutions as positive control. Lysate of a rough, non-invasive *Shigella* mutant (ΔrfbFΔipaBC) lacking the LTB-ST(N12S) construct was used as negative control. Lysates and controls were incubated on plates, and bound LTB was detected with HRP-anti-cholera toxin B subunit (CTB) rabbit polyclonal antibody (Fisher Scientific) and ABTS substrate (Fisher Scientific).

Example 4. ShigETEC Vaccination Provides Serotype-Independent Protection Against *Shigella* Challenge Due to the lack of appropriate diarrhoeal models in small laboratory animals *Shigella* vaccines are typically evaluated for efficacy in the mouse lung model of shigellosis (Van de Verg et al. Infect Immun 1995, 63, 1947-1954). The vaccine potential of ShigETEC was tested in this model upon intranasal immunization of mice three times with two-week intervals. Four weeks after the last immunization animals were infected intranasally with lethal doses of wild-type *Shigella* strains: *S. flexneri* 6 or *S. sonnei* (minimal lethal doses were determined in pilot studies, data not shown).

Vaccination with ShigETEC resulted in 100% protection against both of these heterologous serotype strains (FIG. 4).

Methods: To measure the efficacy of the ShigETEC vaccine, groups of five 6-week-old, female BALB/c mice (Charles River) were vaccinated 3× bi-weekly with ShigETEC intranasally (i.n.) ($10^8$ CFU bacterial suspension in 50 μl PBS/animal). Four weeks after the last vaccination, mice were challenged with minimal lethal doses of either *Shigella sonnei* #598 ($9×10^6$ CFU) or *Shigella flexneri* 6 #542 ($1.2×10^7$ CFU). Minimal lethal doses used were titrated in pilot experiments. Survival was monitored for 14 days post challenge.

Example 5: ShigETEC Vaccination Induces Systemic and Mucosal Antibody Responses Against Shigellae and ETEC Toxins The antibody response to ShigETEC vaccination was evaluated in mice after 1-, 2- or 3-time intranasal immunization(s). To evaluate systemic antibody responses against *Shigella* and the ETEC antigens LTB and ST, we measured serum IgG antibodies by ELISA. IgG levels against ShigETEC lysate were detected already after the first vaccination, which increased with the number of vaccinations (FIG. 5*a*, left panel). Antibodies against LTB and ST were detectable only after two vaccinations and with high variations between individual animals (FIG. 5*a*, middle and right panels). Anti-ST IgG antibody levels were expectedly low, however were clearly induced after 3 immunizations in 44% of animals with levels 4-fold and in 83% of animals with levels 2-fold over individual pre-immunization levels.

Bronchoalveolar lavages (BAL) were collected from animals after three times intranasal immunization and subsequent challenge with heterologous *Shigella* strains 2 weeks after the challenge. Mucosal antibody responses were also detected for anti-*Shigella*, anti-LTB and anti-ST IgA antibodies. Anti-ShigETEC and anti-LTB IgA antibodies were detectable in BAL indicating a specific adaptive response. (FIG. 5*b*).

Methods: To monitor ShigETEC-induced systemic IgG and mucosal IgA responses, mice were vaccinated 3 times i.n. with $10^8$ CFU of the vaccine strain, and serum was taken two weeks after the first and second vaccination and four weeks after the last immunization. Bronchoalveolar lavages (BAL) were performed terminally 14 days after challenge. Specific IgG and IgA antibody levels were measured from sera or BAL, respectively, against ShigETEC lysate (prepared from overnight cultures of ShigETEC with $1×10^7$ CFU/well) or recombinant LTB (Sigma-Aldrich, 100 ng/well) coated on ELISA plates. Biotinylated ST (synthesized by PepScan) was coated at 100 ng/well on streptavidin pre-coated plates (Fisher Scientific). IgG was detected with peroxidase AffiniPure F(ab')₂ Fragment Goat Anti-Mouse IgG (H+L) (Jackson ImmunoResearch), and IgA was detected with peroxidase conjugate goat anti-mouse IgA (Sigma-Aldrich) and ABTS substrate (Fisher Scientific).

Example 6: ShigETEC Vaccination Induces Neutralizing Anti-ETEC Toxin Antibodies In order to provide protection against ETEC, a vaccine should elicit anti-LT and anti-ST antibodies with toxin neutralizing capacities. After 3 times intranasal immunization with ShigETEC we saw induction of anti-LTB and anti-ST IgG in serum. The ability of the vaccine-induced antibodies to block binding of LT to its receptor GM1 was tested in a cell-free ELISA-based assay. We observed serum- and LT-concentration dependent inhibition (FIG. 6a). Serum antibodies were also able to inhibit the LT-induced cAMP release from T84 human colon epithelial cells (FIG. 6b). To prove that the LTB-ST(N12S) fusion protein as expressed by ShigETEC (FIG. 3a) could potentially raise anti-ST neutralizing antibodies, we performed parenteral vaccination with recombinant LTB-ST(N12S) or LTB-ST (wild-type ST) fusion proteins, which induced high anti-ST IgG levels in serum. Those serum antibodies could completely neutralize ST-induced cGMP release in T84 human colon epithelial cells (FIG. 6c). Antibodies raised against LTB-ST(N12S) were capable of neutralizing wild-type ST in the same manner as antibodies raised against LTB-wild type ST confirming that antibodies raised against the mutant ST can functionally neutralize wild type ETEC ST. These data confirm that the LTB-ST(N12S) fusion protein as expressed from the invasion plasmid of ShigETEC can induce an antibody response capable of efficiently neutralizing both ETEC LT and ST.

Methods: ELISA-based LT neutralization assay: Serum from mice vaccinated three times with ShigETEC i.n. was incubated at 2-, 10- and 50-fold dilution with 10, 25, 50 or 100 ng of LT. The amount of LT that remained free from antibody binding was measured on GM1-coated ELISA plates as described above using anti-cholera toxin beta antibody for detection.

Cell-based LT and ST neutralization assay: T84 human colon epithelial cells (ATCC) were seeded in 24 well plates in 1 ml DMEM/F12 (5% FCS, P/S) and grown until confluency. Medium was changed one day before the experiment. Cells were washed 3 times with medium (DMEM/F12 without FCS, P/S) and pre-incubated with medium containing 1 mM 3-3-isobutyl-1-methylxanthine (IBMX, Sigma-Aldrich). 5 ng recombinant LT or synthetic ST (PepScan) were pre-incubated with serum from mock or ShigETEC vaccinated mice (combined pools of individuals with high LTB titers after 3×i.n. immunization, or combined pools of individuals with high ST titers after 3×i.p. vaccination with 200 µg recombinant LTB-ST(N12S) protein). After pre-incubation of toxin and serum, the mix was transferred to T84 cells and incubated at 37° C. (5% $CO_2$) for 3 h. Supernatants were removed, and cells lysed with 0.1 M HCl/1% Triton X-100 at RT. Cell lysates were centrifuged and supernatants were assessed for LT-induced cAMP or ST-induced cGMP by using direct cAMP or cGMP ELISA kits (Enzo Life Sciences), respectively, according to manufacturer's instructions.

Expression of ST Mutants in *Escherichia coli*

Generation of constructs: pET24a(+)-pre-pro-ST construct was generated by amplifying pre-pro-ST gene from ETEC H10407 strain using NdeI-ST-prev (5'-CCCCGA-TATACATATGAAAAAATC-3' (SEQ ID NO:22)) and ST-BamHI-pfw (5'-TCGCGGATCCT-TAATAGCACCCGGTAC-3' (SEQ ID NO:23)) primers and inserting into pET24a(+) expression vector in between BamHI and NdeI restriction sites. pET24a(+)-pre-pro-ST (N12S) was generated via site directed mutagenesis of the pET24a(+)-ST vector, using ST-Mut-P-fw (5'-AAGCAG-GagaACAACACAATTCAC-3' (SEQ ID NO:24) and ST-Mut-P-rev (5'-GTACCGGGTGCTATTAAGGATC-3' (SEQ ID NO:25)) primers. ST sequences in the vectors were confirmed using Sanger Sequencing. Both vectors, as well as pET24a(+) empty vector were further transformed into DE3-Tuner expression cells. ST and ST(N12S) peptide expression: Overnight cultures of DE3-Tuner cells with pET24a(+), pET24a(+)-pre-pro-ST or pET24a(+)-pre-pro-ST(N12S) vectors were diluted and grown to $OD_{600 \, nm}$ 1 at 37° C. at 200 rpm in RPMI containing 1% Casamino Acids and 25 µg/ml Kanamycin. Thereafter, expression of peptides was induced using 1 mM IPTG at 37° C. for 4 hours at 250 rpm. Cells were centrifuged at 5000 rpm for 10 min and the culture supernatant was collected and filtrated using 0.2 µm cellulose-acetate sterile filter.

Verification of ST peptide expression and detoxification of the ST(N12S) peptide: T84 human colon epithelial cells (ATCC) were seeded in 24 well plates in 1 ml DMEM/F12 (5% FCS, P/S) and grown until confluency. Medium was changed one day before the experiment. Cells were washed 3 times with medium (DMEM/F12 without FCS, P/S) and pre-incubated with medium containing 1 mM IBMX. Synthetic ST (PepScan) dilutions were prepared at 100 ng, 25 ng, and 5 ng in DMEM/F12 and incubated on T84 cells at 37° C./5% $CO_2$ for 1 h. Additionally, filtered culture supernatants after ST or ST(N12S) peptide expression from *E. coli* cells were tested at 200 µl/well. After incubation, supernatants were removed, and cells lysed in 0.1 M HCl/1% Triton X-100. Cell lysates were centrifuged, and supernatants assessed for cGMP induction by direct cGMP ELISA (Enzo Life Sciences) according to manufacturer's instructions.

Example 7: Tolerability of ShigETEC

To assess the safety and tolerability of high doses of ShigETEC vaccine, a placebo controlled, double-blinded Phase 1 clinical study was conducted including 84 healthy adults (18-45 years). Primary outcome measure was the evaluation of local and systemic reactions with focus on gastrointestinal symptoms associated with *Shigella* infection. This is differentiated between acute safety (days 1 to 6 following immunization) and overall safety (from day 7 through day 60 following immunization). It was found that single doses of 1×10E9, 1×10E10, 5×10E10 and 2×10E11 CFU as well as multiple doses (2-, 3- and 4-times given at 3-day intervals) of the 5×10E10 CFU dose were generally safe and well tolerated. Oral administration of the high dose ShigETEC vaccine did not raise newly identified safety concerns, and there were no meaningful changes in the previously identified safety profile related to expected symptoms and/or adverse reactions. Twenty-five adverse events were noted in total. There were 14 cases of reactogenicity, and 11 other adverse events reported in the study, all graded as mild or moderate. All of them were resolved by the end of the study. There were no laboratory abnormalities attributed to the vaccine, no serious adverse event (SAE) reported overall in the study and no worsening of any medical condition present at screening through 60 days following the last dose of vaccine in any participants.

Specific description of reactogenicity events: In total, fourteen events were considered as related to the vaccine and assessed as reactogenicity. Thirteen cases were reported as mild, one as moderate and all events recovered/resolved. In Stage 1 (administration of a single dose), the highest dose of 2×10^11 CFU was associated with mild and transient gastrointestinal symptoms in 2 of 8 vaccine recipients. One participant experienced diarrhoea and nausea and a second participant had vomiting. No vaccine recipients experienced evidence of shigellosis. In Stage 2 (multiple administration of the Maximum Tolerated Dose: 5×10E10 CFU), the vaccine was well tolerated across the three multidose regimens (2-, 3-, 4-times).

In the two-dose group one out of 8 vaccine recipients reported nausea on the vaccination day. In the three-dose group a total of five reactogenicity events were reported, all on the vaccination day. Four events were reported for one participant (nausea and vomiting, two times each). Another participant reported vomiting once. In the four-dose group only one participant experienced reactogenicity events, having vomiting on the vaccination days of all four doses and having diarrhoea one day after the last vaccination. In both Stage 1 and Stage 2, all reactogenicity events resolved within one day. No reactogenicity adverse event occurred in the placebo groups.

Specific description of non-reactogenicity events: Eleven non-reactogenicity events occurred. There were six non-reactogenicity adverse events in Stage I and five in Stage II. Nine of them were assessed as mild, two as moderate and none as severe. All events were considered unrelated to the vaccine, and all recovered/resolved by the end of the study.

There were no serious adverse events or severe adverse events during the study. Also, no worsening of medical history was reported.

Methods: This Phase 1 safety and immunogenicity study used a double-blind, placebo-control design and was conducted in two stages. In Stage 1, a total of 48 subjects (2 vaccine recipients to each placebo recipient) were enrolled sequentially in 4 different ascending dose groups (12 subjects per group) to receive a single oral dose of the ShigETEC vaccine starting at a dose in the first group of 1×10^9 Colony Forming Units (CFU) of vaccine or a placebo. Two sentinel subjects (one vaccine and one placebo) were enrolled for each dose group prior to the enrolment of the remaining subjects in that group. Provided no stopping rules were met through 6 days of follow-up for the sentinel subjects (as reviewed by the SRC), the remainder of the subjects for that group were enrolled and dosed. Provided that no stopping rules were met through 6 days of follow-up for the entire group (as reviewed by the SRC) then the next group was enrolled until all 4 groups were enrolled and evaluated through 6 days of assessment. Stage 1 was conducted in an inpatient hospital setting at a single site through Day 6. Subjects in each group were discharged to outpatient follow-up 6 days after dosing (7 days in hospital) if they were asymptomatic for shigellosis-like illness. Any subject with symptomatic illness would be treated with an appropriate course of antibiotic at the time of discharge. All subjects had available stools (once daily if possible) tested for the presence of the ShigETEC vaccine until at least 2 sequential specimens were negative. If shedding persists through 14 days then the subject would be treated with antibiotics regardless of any symptomatology. All subjects were followed through 60 days following immunization to collect adverse events and blood samples.

The DSMB (Data Safety Monitoring Board) review of the Stage 1 safety data declared that the study could proceed to Stage 2, and an optimal vaccine dose (OVD) of ShigETEC vaccine was defined, Stage 2 of the study began as an outpatient double-blind, placebo-controlled study. In this stage, a total of 36 subjects (2 vaccine recipients to each placebo recipient) were be enrolled in 3 different groups (12 subjects per group). Based on Stage 1 data and DSMB recommendation a vaccine dose of 5×10^10 CFU (2, 3, or 4 doses) was chosen for Stage 2. As noted for Stage 1, the progression between each of the dose regimens was depen-dent on satisfactory safety of the prior dose regimen using the same safety parameters that were used in Stage 1. Choice of the interval between doses was determined from an analysis of the duration of shedding in Stage 1 subjects with the goal to dose at or near the end of the shedding cycle. Safety parameters were met as reviewed by the DSMB, and the optimal dose and schedule of ShigETEC was determined by analysis of the safety and shedding data of each of the immunization doses in Stage 1, and an interval of 3 days between doses (e.g, dosing on days 1, 4, 7 and 10 for four doses) was chosen for Stage 2. Stage 2 was conducted in an outpatient setting.

Adverse Events were defined according to ICH-GCP. The grading system is based on the Common Terminology Criteria for Adverse Events (CTCAE) v5.0, published on Nov. 27, 2017.

Regarding Acute Reactogenicity/Tolerability Assessment, a specific list of signs and symptoms was assessed with participant at 2 hours post-immunization and daily during Stage 1 inpatient stay through 6 days following immunization. In Stage 2 this list of signs and symptoms was assessed with each participant at 2 hours post-immunization prior to discharge from the clinic and then by participants themselves on a diary reminder card through 6 days following their last dose of vaccine. The list of signs and symptoms to be evaluated was: nausea/vomiting, diarrhea, abdominal pain, loss of appetite, headache, fatigue, myalgia, illness or clinical adverse event (as defined according to applicable regulations).

The safety reporting window was defined as initiating on the day of immunization through 60 days following the last dose of vaccine/placebo received by a participant.

In the absence of unresolved AEs, for Stage 1, since there was only a single dose given to each participant this was 60 days following immunization. Similarly, for Stage 2 this varied by group and by the interval between dosing. At a minimum, this interval lasted from 92 days up to 110 days.

All adverse events were resolved in the defined follow-up period. There were no dropouts due to Adverse Events.

Acute Safety was defined as specific events associated with acute gastrointestinal and systemic illness symptoms on days 1 to 6 following immunization(s): including nausea, vomiting, diarrhea, abdominal pain, fever, muscle/joint aches, fatigue/malaise, headache, loss of appetite.

Reactogenicity was defined as the number and proportion of expected acute safety period signs and symptom along with their associated toxicity grades. Reactogenicity events in Stage 1 were recorded by site personnel during the inpatient phase of the study. Reactogenicity events in Stage 2 were recorded on a reminder diary card by participants at their primary residence (outpatient) and reviewed on Day 10 with study staff for recording in the database. Unexpected events during the acute safety review are recorded as Adverse Events (AEs).

Example 8: Immunogenicity of High Doses of ShigETEC in Human Volunteers

The immune response of vaccinees was assessed from serum samples obtained at different timepoints following the last immunization (day 6, day 10 and day 28). Immunore-activity was measured in ELISA against the lysed vaccine strain as well as LTB in order to assess the response to the *Shigella* antigens as well as to the heterologously expressed ETEC toxoid fusion protein, respectively. A more than 4-fold increase relative to the corresponding pre-immune serum samples at any timepoint of the post-immune sera was considered significant. The number of seroconverted individuals (percent in parentheses) in the different vaccine cohorts are summarized in Table 1.

Seroconversion rates and the amounts of antibodies showed an increasing tendency proportional to the vaccine dose (in Stage 1) as well as the number of vaccine doses received (Stage 2) (Table 1, FIG. 8). No increase in GMT (geometric mean titer) at the group level was observed for the $1\times10^9$ and $1\times10^{10}$ CFU cohorts, but only for the two higher doses ($5\times10^{10}$ and $2\times10^{11}$ CFU) when the vaccine was applied once (FIG. 8A). Upon multiple administration of the vaccine (at a dose of $5\times10^{10}$ each) a proportional increase of GMT to the number of immunizations was found (FIG. 5B).

Immune response to LTB was only detected at the highest vaccination dose ($2\times10^{11}$) upon single immunizations. In case of multiple vaccinations with $5\times10^{10}$ CFU each, no significant response (i.e., 4-fold increase to baseline levels) to LTB could be detected up to 3 immunizations. However, from the cohort receiving 4 vaccine doses, 50% of the vaccinees (4 out of 8) showed seroconversion to this antigen. This suggests that a high dose of the vaccine strain, preferably given at multiple times, is required to mount an antibody response to the heterologous antigen(s).

TABLE 1

Number (percent) of vaccinees in different cohorts that showed >4-fold seroconversion to ShigETEC lysate

| | group | dose | number of doses | number of subjects and (%) with at least 4-fold increase |
|---|---|---|---|---|
| | placebo | — | 1 to 4 | 0/28 (0%) |
| stage 1 | 1A | $1\times10^9$ | 1 | 0/8 (0%) |
| | 1B | $1\times10^{10}$ | 1 | 1/8 (12.5%) |
| | 1C | $5\times10^{10}$ | 1 | 7/8 (87.5%) |
| | 1D | $2\times10^{11}$ | 1 | 7/8 (87.5%) |
| stage 2 | 2A | $5\times10^{10}$ | 2 | 6/8 (75%) |
| | 2B | $5\times10^{10}$ | 3 | 7/8 (87.5%) |
| | 2C | $5\times10^{10}$ | 4 | 8/8 (100%) |

The invention claimed is:

1. A *Shigella* vaccine comprising $10^8$-$10^{12}$ CFU of a live, genetically attenuated *Shigella flexneri* strain which is of the genotype *Shigella flexneri* 2457TΔrfbFΔipaBCΔinfAΔsetBA::infA-3x(LTB-ST (N12S)).

2. The vaccine of claim 1, wherein the *Shigella flexneri* strain is provided in a pharmaceutical preparation comprising an oral or mucosal formulation.

3. A method of treating a subject to induce an immune response against an infection by *Shigella* and against entero-toxigenic *Escherichia coli*, by oral administration of a vaccine of $10^8$-$10^{12}$ CFU of a live, genetically attenuated *Shigella flexneri* strain which is of the genotype *Shigella flexneri* 2457TΔrfbFΔipaBCΔinfAΔsetBA::infA-3x(LTB-ST (N12S)).

4. The method of claim 3, wherein the treatment induces an immune response in serum, mucosa and/or feces.

5. The method of claim 3, wherein said infection by *Shigella* is any one or more of an infection by *S. flexneri, S. sonnei, S. dysentheriae* or *S. boydii* strains.

6. The vaccine of claim 1, which comprises $10^9$-$10^{12}$ CFU of the live, genetically attenuated *Shigella flexneri* strain.

7. The vaccine of claim 1, wherein the *Shigella flexneri* strain is provided as a liquid, powder, or tablet.

8. The method of claim 3, wherein the vaccine comprises $10^9$-$10^{12}$ CFU of the live, genetically attenuated *Shigella flexneri* strain.

9. The method of claim 3, wherein the vaccine is administered as a liquid, powder, or tablet.

10. The method of claim 3, wherein the vaccine is administered multiple times.

11. The method of claim 4, wherein the treatment induces specific IgA, IgG and/or IgM antibodies.

\* \* \* \* \*

SEQUENCE LISTING

```
<160> NUMBER OF SEQ ID NOS: 25

<210> SEQ ID NO 1
<211> LENGTH: 19
<212> TYPE: PRT
<213> ORGANISM: Artificial Sequence
<220> FEATURE:
<223> OTHER INFORMATION: STm
<220> FEATURE:
<221> NAME/KEY: X
<222> LOCATION: (12)..(12)
<223> OTHER INFORMATION: S, N, K or R
<220> FEATURE:
<221> NAME/KEY: X
<222> LOCATION: (13)..(13)
<223> OTHER INFORMATION: P, G, L or F

<400> SEQUENCE: 1

Asn Ser Ser Asn Tyr Cys Cys Glu Leu Cys Cys Xaa Xaa Ala Cys Thr
1               5                   10                  15

Gly Cys Tyr

<210> SEQ ID NO 2
<211> LENGTH: 19
<212> TYPE: PRT
<213> ORGANISM: E. coli

<400> SEQUENCE: 2

Asn Ser Ser Asn Tyr Cys Cys Glu Leu Cys Cys Asn Pro Ala Cys Thr
1               5                   10                  15

Gly Cys Tyr

<210> SEQ ID NO 3
<211> LENGTH: 124
<212> TYPE: PRT
<213> ORGANISM: E. coli

<400> SEQUENCE: 3

Met Asn Lys Val Lys Cys Tyr Val Leu Phe Thr Ala Leu Pro Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
```

-continued

```
       35                40                45

Thr Glu Ser Met Ala Gly Lys Arg Glu Met Val Ile Ile Thr Phe Lys
   50                55                60

Ser Gly Ala Thr Phe Gln Val Glu Val Pro Gly Ser Gln His Ile Asp
65                70                75                80

Ser Gln Lys Lys Ala Ile Glu Arg Met Lys Asp Thr Leu Arg Ile Thr
            85                90                95

Tyr Leu Thr Glu Thr Lys Ile Asp Lys Leu Cys Val Trp Asn Asn Lys
            100               105               110

Thr Pro Asn Ser Ile Ala Ala Ile Ser Met Glu Asn
         115               120
```

```
<210> SEQ ID NO 4
<211> LENGTH: 19
<212> TYPE: PRT
<213> ORGANISM: Artificial Sequence
<220> FEATURE:
<223> OTHER INFORMATION: STm

<400> SEQUENCE: 4

Asn Ser Ser Asn Tyr Cys Cys Glu Leu Cys Cys Ser Pro Ala Cys Thr
1               5                10                15

Gly Cys Tyr
```

```
<210> SEQ ID NO 5
<211> LENGTH: 19
<212> TYPE: PRT
<213> ORGANISM: Artificial Sequence
<220> FEATURE:
<223> OTHER INFORMATION: STm

<400> SEQUENCE: 5

Asn Ser Ser Asn Tyr Cys Cys Glu Leu Cys Cys Lys Pro Ala Cys Thr
1               5                10                15

Gly Cys Tyr
```

```
<210> SEQ ID NO 6
<211> LENGTH: 19
<212> TYPE: PRT
<213> ORGANISM: Artificial Sequence
<220> FEATURE:
<223> OTHER INFORMATION: STm

<400> SEQUENCE: 6

Asn Ser Ser Asn Tyr Cys Cys Glu Leu Cys Cys Arg Pro Ala Cys Thr
1               5                10                15

Gly Cys Tyr
```

```
<210> SEQ ID NO 7
<211> LENGTH: 19
<212> TYPE: PRT
<213> ORGANISM: Artificial Sequence
<220> FEATURE:
<223> OTHER INFORMATION: STm

<400> SEQUENCE: 7

Asn Ser Ser Asn Tyr Cys Cys Glu Leu Cys Cys Asn Gly Ala Cys Thr
1               5                10                15

Gly Cys Tyr
```

```
<210> SEQ ID NO 8
```

```
<211> LENGTH: 19
<212> TYPE: PRT
<213> ORGANISM: Artificial Sequence
<220> FEATURE:
<223> OTHER INFORMATION: STm

<400> SEQUENCE: 8

Asn Ser Ser Asn Tyr Cys Cys Glu Leu Cys Cys Asn Leu Ala Cys Thr
1               5                   10                  15

Gly Cys Tyr

<210> SEQ ID NO 9
<211> LENGTH: 19
<212> TYPE: PRT
<213> ORGANISM: Artificial Sequence
<220> FEATURE:
<223> OTHER INFORMATION: STm

<400> SEQUENCE: 9

Asn Ser Ser Asn Tyr Cys Cys Glu Leu Cys Cys Asn Phe Ala Cys Thr
1               5                   10                  15

Gly Cys Tyr

<210> SEQ ID NO 10
<211> LENGTH: 143
<212> TYPE: PRT
<213> ORGANISM: Artificial Sequence
<220> FEATURE:
<223> OTHER INFORMATION: LTB-STm
<220> FEATURE:
<221> NAME/KEY: X
<222> LOCATION: (136)..(136)
<223> OTHER INFORMATION: S, N, K or R
<220> FEATURE:
<221> NAME/KEY: X
<222> LOCATION: (137)..(137)
<223> OTHER INFORMATION: P, G, L or F

<400> SEQUENCE: 10

Met Asn Lys Val Lys Cys Tyr Val Leu Phe Thr Ala Leu Pro Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Asn Ser Ser Asn
            115                 120                 125

Tyr Cys Cys Glu Leu Cys Cys Xaa Xaa Ala Cys Thr Gly Cys Tyr
    130                 135                 140

<210> SEQ ID NO 11
<211> LENGTH: 143
<212> TYPE: PRT
<213> ORGANISM: Artificial Sequence
<220> FEATURE:
```

<223> OTHER INFORMATION: LTB-ST(N12S)

<400> SEQUENCE: 11

```
Met Asn Lys Val Lys Cys Tyr Val Leu Phe Thr Ala Leu Pro Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Asn Ser Ser Asn
        115                 120                 125

Tyr Cys Cys Glu Leu Cys Cys Ser Pro Ala Cys Thr Gly Cys Tyr
    130                 135                 140
```

<210> SEQ ID NO 12
<211> LENGTH: 147
<212> TYPE: PRT
<213> ORGANISM: Artificial Sequence
<220> FEATURE:
<223> OTHER INFORMATION: LTB-ST(N12S)

<400> SEQUENCE: 12

```
Met Asn Lys Val Lys Cys Tyr Val Leu Phe Thr Ala Leu Pro Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Gly Pro Gly Pro
        115                 120                 125

Asn Ser Ser Asn Tyr Cys Cys Glu Leu Cys Cys Ser Pro Ala Cys Thr
    130                 135                 140

Gly Cys Tyr
145
```

<210> SEQ ID NO 13
<211> LENGTH: 444
<212> TYPE: DNA
<213> ORGANISM: Artificial Sequence
<220> FEATURE:
<223> OTHER INFORMATION: LTB-ST(N12S)

<400> SEQUENCE: 13
atgaataaag taaaatgtta tgttttattt acggcgttac catcctctct atgtgcatac      60
ggagctcccc agtctattac agaactatgt tcggaatatc gcaacacaca aatatatacg     120
ataaatgaca agatactatc atatacggaa tcgatggcag gcaaaagaga aatggttatc     180 attacatttta agagcggcgc aacatttcag gtcgaagtcc cgggcagtca acatatagac     240
tcccaaaaaa aagccattga aaggatgaag gacacattaa gaatcacata tctgaccgag     300
accaaaattg ataaattatg tgtatggaat aataaaaccc ccaattcaat tgcggcaatc     360
agtatggaaa acgggccggg gcccaattct tctaactact gctgtgaact ttgttgttct     420
cctgcctgta caggatgtta ctag                                           444

<210> SEQ ID NO 14
<211> LENGTH: 432
<212> TYPE: DNA
<213> ORGANISM: Artificial Sequence
<220> FEATURE:
<223> OTHER INFORMATION: LTB-ST(N12S)

<400> SEQUENCE: 14
atgaataaag taaaatgtta tgttttattt acggcgttac catcctctct atgtgcatac      60
ggagctcccc agtctattac agaactatgt tcggaatatc gcaacacaca aatatatacg     120
ataaatgaca agatactatc atatacggaa tcgatggcag gcaaaagaga aatggttatc     180 attacatttta agagcggcgc aacatttcag gtcgaagtcc cgggcagtca acatatagac     240
tcccaaaaaa aagccattga aaggatgaag gacacattaa gaatcacata tctgaccgag     300
accaaaattg ataaattatg tgtatggaat aataaaaccc ccaattcaat tgcggcaatc     360
agtatggaaa acaattcttc taactactgc tgtgaacttt gttgttctcc tgcctgtaca     420
ggatgttact ag                                                        432

<210> SEQ ID NO 15
<211> LENGTH: 249
<212> TYPE: DNA
<213> ORGANISM: E. coli

<400> SEQUENCE: 15
gctgccgtgg ttcaagtcgc gactaataaa aataatcagg ttgccatgat tcaatgtaca      60
cctttctcac attcgtctcc ggcatgaaaa cgatgcactc tttctttatc gctttcacta     120
cacattttat cctcgcatgg atgttttata aaaaacatga ttgacatcat gttgcatata     180
ggttaaacaa aacaagtggc gttatctttt tccggattgt cttcttgtat gatatataag     240
ttttcctcg                                                            249

<210> SEQ ID NO 16
<211> LENGTH: 118
<212> TYPE: DNA
<213> ORGANISM: Artificial Sequence
<220> FEATURE:
<223> OTHER INFORMATION: Terminator

<400> SEQUENCE: 16
tttgctttaa aagcatgtct aatgctagga acctatataa caactactgt acttatacta      60
atgagcctta tgctgcattt gaactaaagc ggccgccaga tcttccggat ggctcgag       118

<210> SEQ ID NO 17
<211> LENGTH: 36

```
<212> TYPE: DNA
<213> ORGANISM: Artificial Sequence
<220> FEATURE:
<223> OTHER INFORMATION: Terminator

<400> SEQUENCE: 17
tttgctttaa aagcatgtct aatgaatccg ctcgag                                36

<210> SEQ ID NO 18
<211> LENGTH: 103
<212> TYPE: DNA
<213> ORGANISM: Artificial Sequence
<220> FEATURE:
<223> OTHER INFORMATION: Terminator

<400> SEQUENCE: 18
tttgctttaa aagcatgtct aatgctagga acctatataa caactactgt acttatacta     60
atgagcctta tgctgcattt gaaaaggcgg tagaggatgc aat                       103

<210> SEQ ID NO 19
<211> LENGTH: 3377
<212> TYPE: DNA
<213> ORGANISM: Artificial Sequence
<220> FEATURE:
<223> OTHER INFORMATION: expression construct

<400> SEQUENCE: 19
gtcgcaaaac atgtcattca ggttcatctc accaataagg atatgagtga agtggaggat     60
aagtgagtct gctgtcagag tttttctggtg tatgtcagta aggataccac ggtgcttgtt    120
ttcaccacaa gaatgaatgt tttcggcaca tttctcccca gagtgttata attgcggtcg     180
cagagttggt tacgctcatt accccgctgc cgataaggaa ttttttcgcgt caggtaacgc    240 ccatcgttta tctcaccgct cccttatacg ttgcgctttt ggtgcggctt agccgtgtgt     300
tttcggagta atgtgccgaa cctgtttgtt gcgatttagc gcgcaaatct ttacttattt     360
acagaacttc ggcattatct tgccggttca aattacggta gtgataccc agaggattag      420 atggccaaag aagacaatat tgaaatgcaa ggtaccgttc ttgaaacgtt gcctaatacc     480
atgttccgcg tagagttaga aaacggtcac gtggttactg cacacatctc cggtaaaatg     540
cgcaaaaact acatccgcat cctgacgggc gacaaagtga ctgttgaact gaccccgtac     600
gacctgagca aaggccgcat tgtcttccgt agtcgctgat tgtttttaccg cctgatgggc    660 gaagagaaag aacgagtaaa aggtcggttt aaccggcctt tttattttgt gatatgtatg     720
aagtactttg gaagtataag tccataactt gtctcgatgt aggcggccgc gctgccgtgg     780
ttcaagtcgc gactaataaa aataatcagg ttgccatgat tcaatgtaca cctttctcac     840
attcgtctcc ggcatgaaaa cgatgcactc tttctttatc gctttcacta cacattttat     900
cctcgcatgg atgtttttata aaaaacatga ttgacatcat gttgcatata ggttaaacaa    960
aacaagtggc gttatctttt tccggattgt cttcttgtat gatatataag ttttcctcga    1020
tgaataaagt aaaatgttat gttttatttta cggcgttacc atcctctcta tgtgcatacg    1080
gagctcccca gtctattaca gaactatgtt cggaatatcg caacacacaa atatatacga    1140
taaatgacaa gatactatca tatacggaat cgatggcagg caaaagagaa atggttatca    1200
ttacatttaa gagcggcgca acatttcagg tcgaagtccc gggcagtcaa catatagact    1260
cccaaaaaaa agccattgaa aggatgaagg acacattaag aatcacatat ctgaccgaga    1320
ccaaaattga taaattatgt gtatggaata ataaaacccc caattcaatt gcggcaatca    1380
```

-continued

```
gtatggaaaa cgggccgggg cccaattctt ctaactactg ctgtgaactt tgttgttctc      1440
ctgcctgtac aggatgttac tagtttgctt taaaagcatg tctaatgcta ggaacctata      1500
taacaactac tgtacttata ctaatgagcc ttatgctgca tttgaactaa agcggccgcc      1560
agatcttccg gatggctcga ggctgccgtg gttcaagtcg cgactaataa aaataatcag      1620
gttgccatga ttcaatgtac acctttctca cattcgtctc cggcatgaaa acgatgcact      1680
ctttctttat cgctttcact acacatttta tcctcgcatg gatgttttat aaaaaacatg      1740
attgacatca tgttgcatat aggttaaaca aaacaagtgg cgttatcttt ttccggattg      1800
tcttcttgta tgatatataa gttttcctcg atgaataaag taaaatgtta tgttttattt      1860
acggcgttac catcctctct atgtgcatac ggagctcccc agtctattac agaactatgt      1920
tcggaatatc gcaacacaca aatatatacg ataaatgaca agatactatc atatacggaa      1980
tcgatggcag gcaaaagaga aatggttatc attacattta agagcggcgc aacatttcag      2040
gtcgaagtcc cggcagtca acatatagac tcccaaaaaa aagccattga aaggatgaag      2100
gacacattaa gaatcacata tctgaccgag accaaaattg ataaattatg tgtatggaat      2160
aataaaaccc ccaattcaat tgcggcaatc agtatggaaa acgggccggg gcccaattct      2220
tctaactact gctgtgaact ttgttgttct cctgcctgta caggatgtta ctagtttgct      2280
ttaaaagcat gtctaatgaa tccgctcgag gctgccgtgg ttcaagtcgc gactaataaa      2340
aataatcagg ttgccatgat tcaatgtaca cctttctcac attcgtctcc ggcatgaaaa      2400
cgatgcactc tttctttatc gctttcacta cacattttat cctcgcatgg atgttttata      2460
aaaaacatga ttgacatcat gttgcatata ggttaaacaa aacaagtggc gttatctttt      2520
tccggattgt cttcttgtat gatatataag ttttcctcga tgaataaagt aaaatgttat      2580
gttttattta cggcgttacc atcctctcta tgtgcatacg gagctcccca gtctattaca      2640
gaactatgtt cggaatatcg caacacacaa atatatacga taaatgacaa gatactatca      2700
tatacggaat cgatggcagg caaaagagaa atggttatca ttacatttaa gagcggcgca      2760
acatttcagg tcgaagtccc gggcagtcaa catatagact cccaaaaaaa agccattgaa      2820
aggatgaagg acacattaag aatcacatat ctgaccgaga ccaaaattga taaattatgt      2880
gtatggaata ataaaaccc caattcaatt gcggcaatca gtatggaaaa cgggccgggg      2940
cccaattctt ctaactactg ctgtgaactt tgttgttctc ctgcctgtac aggatgttac      3000
tagtttgctt taaaagcatg tctaatgcta ggaacctata taacaactac tgtacttata      3060
ctaatgagcc ttatgctgca tttgaaaagg cggtagagga tgcaatgttt aaacgtgtag      3120
gctggagctg cttcgaagtt cctatacttt ctagagaata ggaacttcgg aataggaact      3180
aaggaggata ttcatatgga tgaatgttca ggctatcttt atcttgatgg tggttcagct      3240
gtttggtaaa gaaatcgctg taacaataga agaactgcag gcagtactgg tcccacatcg      3300
tttgctcagt caactggtga agttccgtag cgcgtaaatt aatgctttgc atgaaacgtt      3360
actggagtgg atgaaag                                                    3377
```

<210> SEQ ID NO 20
<211> LENGTH: 4
<212> TYPE: PRT
<213> ORGANISM: Artificial Sequence
<220> FEATURE:
<223> OTHER INFORMATION: Linker

<400> SEQUENCE: 20

Gly Pro Gly Pro

-continued

1

```
<210> SEQ ID NO 21
<211> LENGTH: 25
<212> TYPE: PRT
<213> ORGANISM: Artificial Sequence
<220> FEATURE:
<223> OTHER INFORMATION: STm

<400> SEQUENCE: 21

Glu Asn Gly Pro Gly Pro Asn Ser Ser Asn Tyr Cys Cys Glu Leu Cys
1               5                   10                  15

Cys Ser Pro Ala Cys Thr Gly Cys Tyr
            20                  25

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
ccccgatata catatgaaaa aatc                                    24

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
tcgcggatcc ttaatagcac ccggtac                                27

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
aagcaggaga acaacacaat tcac                                    24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
aagcaggaga acaacacaat tcac                                    24
```